US011033745B2

(12) United States Patent
Edmonson et al.

(10) Patent No.: US 11,033,745 B2
(45) Date of Patent: Jun. 15, 2021

(54) PACEMAKER AND METHOD FOR DELIVERING LEADING PACING PULSES

(71) Applicant: Medtronic, Inc., Minneapolis, MN (US)

(72) Inventors: Jonathan D. Edmonson, Blaine, MN (US); Troy E. Jackson, Rogers, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 259 days.

(21) Appl. No.: 16/171,733

(22) Filed: Oct. 26, 2018

(65) Prior Publication Data

US 2020/0129771 A1 Apr. 30, 2020

(51) Int. Cl.
| | | |
|---|---|---|
| *A61N 1/362* | (2006.01) | |
| *A61N 1/365* | (2006.01) | |
| *A61N 1/37* | (2006.01) | |
| *A61N 1/375* | (2006.01) | |
| *A61N 1/39* | (2006.01) | |

(52) U.S. Cl.
CPC ....... *A61N 1/3706* (2013.01); *A61N 1/36514* (2013.01); *A61N 1/3702* (2013.01); *A61N 1/3956* (2013.01)

(58) Field of Classification Search
CPC .. A61N 1/3706; A61N 1/3956; A61N 1/3627; A61N 1/3756; A61N 1/36514; A61N 1/3702
USPC .................................................. 600/333, 518
See application file for complete search history.

(56) References Cited

U.S. PATENT DOCUMENTS

| | | | |
|---|---|---|---|
| 4,307,725 A | * | 12/1981 | Sowton ................ A61N 1/3621 607/14 |
| 5,507,782 A | | 4/1996 | Kieval et al. |
| 5,683,432 A | | 11/1997 | Goedeke et al. |
| 6,704,602 B2 | | 3/2004 | Berg et al. |
| 6,963,774 B2 | * | 11/2005 | Stahmann ............ A61N 1/3622 607/9 |
| 7,630,767 B1 | | 12/2009 | Poore et al. |
| 8,204,590 B2 | | 6/2012 | Sambelashvili et al. |

(Continued)

FOREIGN PATENT DOCUMENTS

| | | | | |
|---|---|---|---|---|
| EP | 2471452 A1 | * | 7/2012 | .......... A61N 1/3956 |
| EP | 2471452 A1 | | 7/2012 | |

(Continued)

OTHER PUBLICATIONS (PCT/US2019/057448) PCT Notification of Transmittal of the International Search Report and the Written Opinion of the International Searching Authority, dated Mar. 11, 2020, 9 pages.

*Primary Examiner* — Carl H Layno
*Assistant Examiner* — Anh-Khoa N Dinh

(57) ABSTRACT

A pacemaker is configured to deliver pacing pulses that lead pacing pulses delivered by another medical device. The pacemaker may detect pacing pulses delivered by the other medical device by a pulse detector circuit of the pacemaker, produce a pulse detect signal in response to each one of the detected pacing pulses, determine a pulse detect interval between two pulse detect signals consecutively produced by the pulse detector circuit, set a pacing escape interval based on the pulse detect interval less a pre-interval, and deliver a pacing pulse upon expiration of the pacing escape interval.

29 Claims, 11 Drawing Sheets

(56) References Cited

U.S. PATENT DOCUMENTS

| | | | |
|---|---|---|---|
| 8,433,409 B2 | 4/2013 | Johnson et al. | |
| 8,457,742 B2 | 6/2013 | Jacobson | |
| 8,532,785 B1 | 9/2013 | Crutchfield et al. | |
| 8,541,131 B2 | 9/2013 | Lund et al. | |
| 9,233,251 B2 | 1/2016 | Rajan et al. | |
| 9,399,140 B2 | 7/2016 | Cho et al. | |
| 9,775,982 B2 | 10/2017 | Grubac et al. | |
| 9,808,633 B2 | 11/2017 | Bonner et al. | |
| 2007/0088398 A1* | 4/2007 | Jacobson | A61N 1/36514 607/9 |
| 2013/0231710 A1* | 9/2013 | Jacobson | A61N 1/36842 607/4 |
| 2015/0305640 A1 | 10/2015 | Reinke et al. | |
| 2015/0305642 A1 | 10/2015 | Reinke et al. | |
| 2016/0114169 A1* | 4/2016 | Sheldon | A61N 1/3704 607/17 |
| 2018/0117337 A1 | 5/2018 | Demmer et al. | |
| 2018/0154154 A1 | 6/2018 | Sheldon et al. | |

FOREIGN PATENT DOCUMENTS

| | | | |
|---|---|---|---|
| WO | 20150164167 A1 | 10/2015 | |
| WO | 20150164172 A1 | 10/2015 | |

\* cited by examiner

PACEMAKER AND METHOD FOR DELIVERING LEADING PACING PULSES

TECHNICAL FIELD

This disclosure relates to a pacemaker and method for controlling delivery of leading cardiac pacing pulses for promoting synchrony between heart chambers.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (AV) node. The AV node responds by propagating a ventricular depolarization signal through the bundle of His of the ventricular septum and thereafter to the bundle branches and the Purkinje muscle fibers of the right and left ventricles.

Patients with a conduction system abnormality, e.g., poor or slow conduction through the AV node, SA node function, or ventricular conduction system may receive a pacemaker to restore a more normal heart rhythm and synchrony of the heart chamber contractions. Patients experiencing heart failure or symptoms associated with conduction disorders may receive a multi-chamber pacemaker for delivering cardiac resynchronization therapy (CRT). Improving the synchrony and coordination of the heart chamber contractions may improve the pumping efficiency of the heart and can improve symptoms of heart failure.

Multi-chamber pacemakers for providing CRT are available or have been proposed which require three transvenous leads carrying electrodes for sensing and pacing in the right atrium, the right ventricle and the left ventricle. In order to pace and sense in the left ventricle, coronary sinus leads are available or have been proposed. A coronary sinus lead is advanced into a cardiac vein of the left ventricle via the coronary sinus for placing electrodes in proximity to the left ventricular myocardium. Advancement of a pacing lead into the coronary sinus and cardiac veins can be challenging and requires considerable technical expertise and imaging equipment.

Single chamber intracardiac pacemakers are available or have been proposed that are implantable within a ventricular chamber of a patient's heart for delivering ventricular pacing pulses. The intracardiac ventricular pacemaker is a leadless pacemaker that does not require connection to a transvenous pacing lead that may become a pathway for infection or be associated with other complications. While single chamber ventricular sensing and pacing by an intracardiac pacemaker may adequately address some heart rhythm conditions, patients having ventricular dyssynchrony due to heart failure or conduction abnormalities may benefit from a pacemaker system that can deliver CRT without requiring multiple cardiac leads such as a coronary sinus lead.

SUMMARY

The techniques of this disclosure generally relate to a single chamber cardiac pacemaker capable of detecting pacing pulses delivered by another medical device and delivering pacing pulses that precede the detected pacing pulses by a pre-interval. CRT may be provided by delivering ventricular pacing pulses to one ventricular chamber at a pre-interval earlier than ventricular pacing pulses delivered by another medical device to the other ventricular chamber. A pacemaker operating according to the techniques disclosed herein may detect pacing pulses delivered by another medical device, determine time intervals between consecutive pairs of detected pacing pulses and set a pacing escape interval based on the determined time intervals for scheduling each pacing pulse at a pre-interval earlier than the next expected pacing pulse delivered by the other medical device.

In one example, the disclosure provides a pacemaker including a pulse detector circuit, a control circuit and a pulse generator. The pulse detector circuit is configured to detect pacing pulses delivered by another medical device and produce a pulse detect signal in response to each one of the detected pacing pulses. The control circuit is configured to determine a pulse detect interval between two pulse detect signals consecutively received from the pulse detector circuit and set a pacing escape interval based on the pulse detect interval less a pre-interval. The pulse generator is configured to deliver a pacing pulse upon expiration of the pacing escape interval. The control circuit may be further configured to set at least one time window after the delivered pacing pulse. The control circuit may then select a response to the next pulse detect signal received from the pulse detector circuit for controlling delivery of a second pacing pulse based on whether the next pulse detect signal occurs within the time window.

In another example, the disclosure provides a method performed by a pacemaker. The method includes detecting pacing pulses delivered by another medical device, producing a pulse detect signal by a pulse detector circuit in response to each one of the detected pacing pulses, determining a pulse detect interval between two pulse detect signals consecutively produced by the pulse detector circuit, setting a pacing escape interval based on the pulse detect interval less a pre-interval and delivering a pacing pulse upon expiration of the pacing escape interval. The method may further include setting at least one time window after the delivered pacing pulse and selecting a response to a next pulse detect signal received from the pulse detector circuit for controlling delivery of a second pacing pulse based on whether the next pulse detect signal occurs within the time window.

In yet another example, the disclosure provides a non-transitory, computer-readable storage medium comprising a set of instructions which, when executed by a control circuit of a pacemaker, cause the pacemaker to detect pacing pulses delivered by another medical device, produce a pulse detect signal by a pulse detector circuit in response to each one of the detected pacing pulses, determine a pulse detect interval between two pulse detect signals consecutively produced by the pulse detector circuit, set a pacing escape interval based on the pulse detect interval less a pre-interval, and deliver a pacing pulse upon expiration of the pacing escape interval. The instructions may further cause the pacemaker to set at least one time window after the delivered pacing pulse and select a response to a next pulse detect signal received from the pulse detector circuit for controlling delivery of a second pacing pulse based on whether the next pulse detect signal occurs within the time window.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

In general, this disclosure describes a pacemaker and techniques for delivering ventricular pacing pulses to promote an improvement in synchrony between right and left ventricular contractions, e.g., in patient's having compromised ventricular hemodynamic function due to heart failure, cardiomyopathy, abnormal ventricular conduction or other abnormalities. In particular, a leadless intracardiac pacemaker is disclosed that is capable of delivering pacing pulses in one ventricle that lead ventricular pacing pulses delivered in another ventricle by another medical device, e.g., a second pacemaker implanted in the patient. In some patients, one ventricular contraction lags the other ventricle resulting in uncoordinated ventricular contraction and less efficient ejection of blood from the ventricles compared to a normally functioning heart. Resynchronization of the ventricles by delivering pacing pulses to one ventricle earlier than the other ventricle can improve the hemodynamic function of the heart. The techniques disclosed herein improve the operation of a leadless, intracardiac pacemaker in delivering a pacing therapy by enabling the pacemaker to deliver CRT pacing pulses in a first ventricle that lead pacing pulses delivered in a second ventricle by another medical device without requiring an additional transvenous lead in the first ventricular chamber and without requiring the two devices to be in wired or wireless communication with each other for coordinating CRT pacing pulses.

Figure 1:
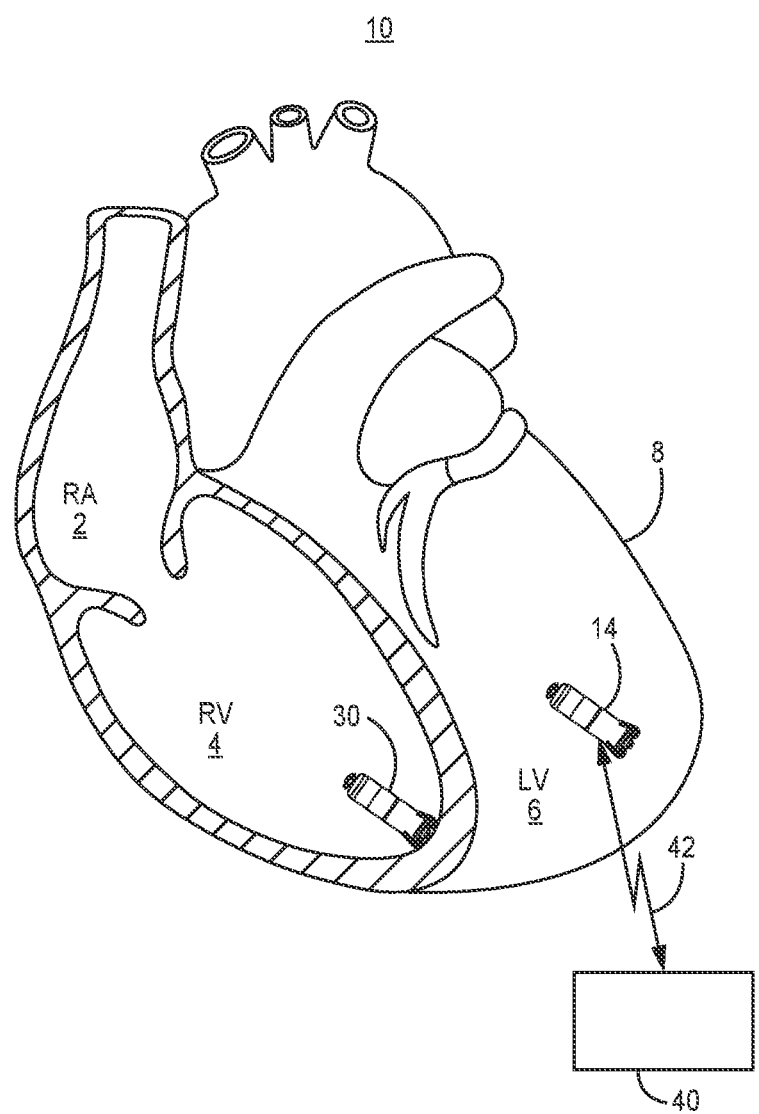
FIG. 1 is a conceptual diagram illustrating an implantable medical device (IMD) system that may be used to deliver cardiac resynchronization pacing pulses to a patient's heart.

FIG. 1 is a conceptual diagram illustrating an implantable medical device (IMD) system 10 that may be used to deliver cardiac resynchronization pacing pulses to a patient's heart 8. IMD system 10 includes an intracardiac ventricular pacemaker 14 shown in the left ventricle (LV) 6 for sensing LV cardiac electrical signals and delivering LV pacing pulses. IMD system 10 may further include a second intracardiac ventricular pacemaker 30 shown in the right ventricle (RV) 4 of heart 8. RV pacemaker 30 is configured to sense RV cardiac electrical signals, deliver RV pacing pulses, and may be configured to sense atrial events to provide atrial synchronized ventricular pacing to the RV 4.

As disclosed herein, LV pacemaker 14 is configured to detect pacing pulses delivered by RV pacemaker 30 and schedule LV pacing pulses relative to the detected RV pacing pulses to promote ventricular synchrony. In particular, LV pacemaker 14 is capable of scheduling LV pacing pulses at a pre-interval earlier than an anticipated RV pacing pulse in order to deliver biventricular pacing that includes LV pacing pulses that lead the RV pacing pulses. The RV pacing pulses may be synchronized to atrial events that are sensed by RV pacemaker 30.

Pacemakers 14 and 30 may be transcatheter intracardiac pacemakers adapted for implantation wholly within a heart chamber, e.g., wholly within the LV 6 and wholly within the RV 4, respectively. Pacemakers 14 and 30 may be reduced in size compared to subcutaneously implanted pacemakers and may be generally cylindrical in shape to enable transvenous implantation in a heart chamber via a delivery catheter.

In the example shown, pacemaker 14 is shown near the apex of LV 6, e.g., positioned along an endocardial wall of the LV 6. RV pacemaker 30 is shown positioned along the endocardial wall near the apex of the RV 4. The techniques disclosed herein are not limited to the pacemaker locations shown in the example of FIG. 1 and other positions within or outside heart 8 are possible. For example, pacemaker 14 performing the techniques disclosed herein may be positioned at other endocardial or epicardial locations in or on the LV 6 for detecting RV pacing pulses delivered by RV pacemaker 30 (in or on RV 4) and delivering LV leading pacing pulses at a pre-interval earlier than an expected RV pacing pulse. For example, pacemaker 14 may be positioned endocardially or epicardially along the lateral wall, inferior wall, anterior wall or posterior wall of the heart, and may be placed near the apex or superior to the apex.

In the illustrative examples described herein, LV pacemaker 14 is described as being configured to detect RV pacing pulses delivered by RV pacemaker 30 and scheduling leading LV pacing pulses to provide LV leading biventricular pacing by system 10. In some cases, a patient may require RV leading pacing in which case RV pacemaker 30 may be configured to operate according to the techniques disclosed herein for generating RV pacing pulses at a pre-interval earlier than LV pacing pulses delivered by LV pacemaker 14. The examples of LV-leading biventricular pacing presented herein are illustrative and not intended to limit the disclosed techniques to an LV pacemaker. The techniques may be implemented in a pacemaker positioned in or on another heart chamber to provide pacing pulses that lead an expected pacing pulse delivered by another medical device to another heart chamber or another location of the same heart chamber.

Both pacemakers 14 and 30 are capable of producing electrical stimulation pulses, e.g., pacing pulses, delivered to the respective LV 6 and RV 4 via one or more electrodes on the outer housing of the pacemaker, referred to herein as "housing based electrodes." Both pacemakers 14 and 30 may be configured to sense a cardiac electrical signal from the respective LV 6 and RV 4 using the housing based electrodes for detecting ventricular R-waves attendant to ventricular depolarization for producing a ventricular electrogram (EGM) signal. The cardiac electrical signals may be sensed using the housing based electrodes that are also used to deliver pacing pulses to the heart 8.

RV pacemaker 30 may be configured to control the delivery of ventricular pacing pulses to the RV 4 in an atrial synchronous ventricular pacing mode that promotes synchrony between atrial contractions and ventricular contractions, e.g., in a patient with atrioventricular (AV) block. In some examples, RV pacemaker 30 senses atrial events from an intraventricular cardiac motion signal produced by a motion sensor, such as an accelerometer, included in RV pacemaker 30. An accelerometer included in RV pacemaker 30 may produce a cardiac motion signal including an atrial mechanical systole signal representing the contraction or "atrial kick" of right atrium (RA) 2. RV pacemaker 30 may deliver RV pacing pulses at a programmed AV interval after a sensed atrial systolic mechanical event sensed from the motion sensor. The atrial synchronous ventricular pacing mode may be referred to as a "VDD" pacing mode since single chamber ventricular pacing is being delivered with dual chamber sensing and a dual response is provided to sensed events, either a pacing pulse is triggered in response to an atrial sensed event or inhibited in response to an intrinsic ventricular sensed event, e.g., an R-wave. RV pacemaker 30 may correspond to examples of leadless, intracardiac ventricular pacemakers capable of atrial synchronized ventricular pacing as generally disclosed in U.S. Pat. No. 9,399,140 (Cho, et al.) and in pre-grant U.S. Publication No. 2018/0117337 (Demmer, et al.), both incorporated herein by reference in their entirety.

Pacemakers 14 and 30 may be capable of bidirectional wireless communication with an external device 40 for programming pacing and sensing control parameters. Aspects of external device 40 may generally correspond to the external programming/monitoring unit disclosed in U.S. Pat. No. 5,507,782 (Kieval, et al.), hereby incorporated herein by reference in its entirety. External device 40 is often referred to as a "programmer" because it is typically used by a physician, technician, nurse, clinician or other qualified user for programming operating parameters in pacemaker 14 (and/or 30). External device 40 may be located in a clinic, hospital or other medical facility. External device 40 may alternatively be embodied as a home monitor or a handheld device that may be used in a medical facility, in the patient's home, or another location.

External device 40 is configured for bidirectional communication with implantable telemetry circuitry included in pacemakers 14 and 30. External device 40 is shown with a wireless communication link 42 established with pacemaker 14. Communication link 42 may be established using a radio frequency (RF) link such as BLUETOOTH®, Wi-Fi, Medical Implant Communication Service (MICS) or other communication bandwidth. In some examples, external device 40 may include a programming head that is placed proximate pacemaker 14 to establish and maintain a communication link 42. In other examples external device 40 and pacemaker 14 may be configured to communicate using a distance telemetry algorithm and circuitry that does not require the use of a programming head and does not require user intervention to maintain a wireless communication link. An example RF telemetry communication system that may be implemented in system 10 is generally disclosed in U.S. Pat. No. 5,683,432 (Goedeke, et al.), hereby incorporated herein by reference in its entirety. External device 40 may display data and information relating to pacemaker functions to a user for reviewing pacemaker operation and programmed parameters.

It is contemplated that external device 40 may be in wired or wireless connection to a communications network via a telemetry circuit that includes a transceiver and antenna or via a hardwired communication line for transferring data to a centralized database or computer to allow remote management of the patient. Remote patient management systems including a remote patient database may be configured to utilize the presently disclosed techniques to enable a clinician to review EGM, motion signals, and pacing pulse detect signal and pacing signals displayed as marker channel data and authorize programming of sensing and therapy control parameters in pacemakers 14 and 30, e.g., after viewing a visual representation of EGM, motion signals and marker channel data. External device 40 may be a MYCARE-LINK™ Patient Monitor available from Medtronic, Inc. Minneapolis Minn., USA, in one example.

Figure 2:
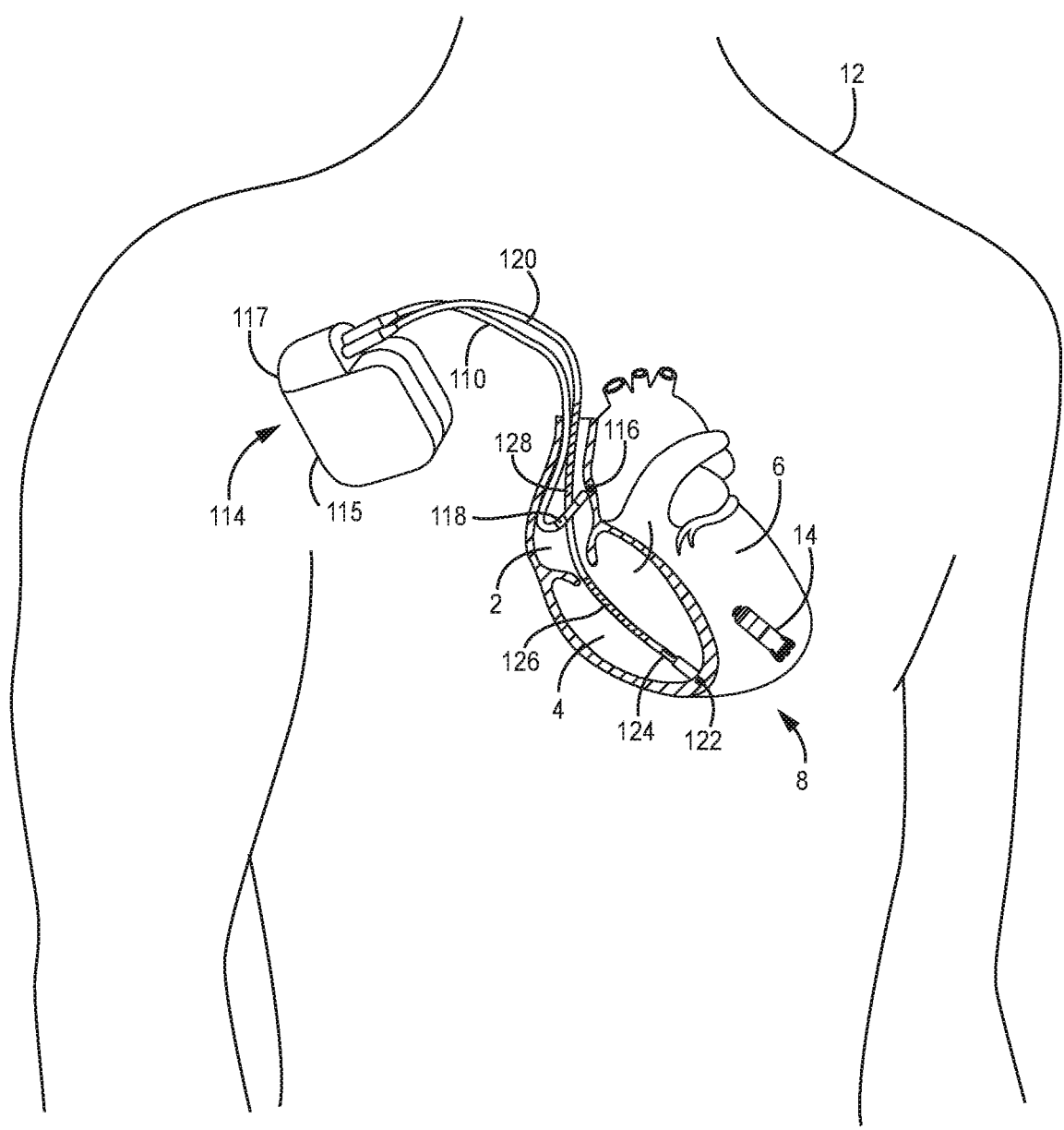
FIG. 2 is a conceptual diagram of another example of an IMD system that may be used to deliver cardiac resynchronization pacing pulses to a patient's heart.

FIG. 2 is a conceptual diagram of an IMD system 100 including pacemaker 14 for delivering LV leading pacing pulses according to another example. IMD system 100 may include a dual chamber pacemaker or implantable cardioverter defibrillator (ICD) 114 and leadless, intra-cardiac LV pacemaker 14. Dual chamber ICD 114 is shown coupled to transvenous leads 110 and 120 in communication with the RA 2 and RV 4, respectively, of heart 8. ICD 114 is configured to sense cardiac electrical signals and deliver electrical stimulation pulses in the RA 2 and the RV 4. ICD 114 includes a housing 115 enclosing electronic circuitry, e.g., a cardiac electrical signal sensing circuit, therapy delivery circuit, control circuit, memory, telemetry circuit, other optional sensors, and a power source. ICD 114 is shown implanted in a right pectoral position in FIG. 2, however it is recognized that ICD 114 may be implanted in other locations, e.g., in a left pectoral position, particularly when ICD 114 includes cardioversion and defibrillation (CV/DF) capabilities using housing 115 as an active electrode.

ICD 114 has a connector assembly 117 for receiving proximal connectors of RA lead 110 and RV lead 120. RA lead 110 may carry a distal tip electrode 116 and ring electrode 118 for sensing atrial signals, e.g., P-waves attendant to atrial depolarization, and delivering RA pacing pulses. RV lead 120 may carry pacing and sensing electrodes 122 and 124 for sensing ventricular signals in the RV, e.g., R-waves attendant to RV depolarization, and for delivering RV pacing pulses. RV lead 120 may also carry RV defibrillation electrode 126 and a superior vena cava (SVC) defibrillation electrode 128. Defibrillation electrodes 126 and 128 are shown as coil electrodes spaced apart proximally from the distal pacing and sensing electrodes 122 and 124 and may be used for delivering high voltage CV/DF shock pulses.

ICD 114 may be configured to provide dual chamber sensing and pacing in RA 2 and RV 4. The control circuit of ICD 114 may set an AV pacing interval following each atrial pacing pulse delivered using RA lead 110 and following each intrinsic P-wave sensed in RA 2 for controlling the timing of pacing pulses delivered to RV 4 in an atrial synchronized ventricular pacing mode, e.g., a DDD pacing mode. LV pacemaker 14 may be positioned in LV 6 for sensing left ventricular signals, e.g., R-waves attendant to left ventricular depolarizations, and for delivering pacing pulses to LV 6. IMD system 100 may be configured to deliver multi-chamber pacing therapies such as CRT through coordinated delivery of RA pacing pulses, RV pacing pulses and LV pacing pulses. Using the techniques disclosed herein, LV pacemaker 14 may detect RV pacing pulses delivered to RV 4 by ICD 114 and determine RV-RV intervals as time intervals between two consecutively detected RV pacing pulses. Based on the RV-RV intervals, LV pacemaker 14 may set LV pacing escape intervals to deliver LV pacing pulses that lead RV pacing pulses by a VV interval, also referred to herein as "pre-interval" when LV 6 is paced earlier than RV 4 during a given cardiac cycle. The LV pacing escape interval is the time interval that is set by pacemaker 14 in response to detecting an RV pacing pulse delivered by another medical device, e.g., RV pacemaker 30 or ICD 114, and counted down or timed out until its expiration, at which point an LV pacing pulse is delivered. The LV pacing escape interval is therefore the time interval from an RV pacing pulse detection until delivery of an LV pacing pulse. The pre-interval is the time interval from the delivered LV pacing pulse to the time that the next RV pacing pulse is expected to be detected and represents a desired LV-RV interval during biventricular pacing to promote ventricular synchrony.

In other examples, a medical device system incorporating the techniques disclosed herein may include a single chamber, RV pacemaker or ICD coupled to a single transvenous lead for delivering RV pacing pulses instead of the dual chamber ICD 114 shown in FIG. 2 having both an atrial and ventricular lead. In general LV pacemaker 14 may be co-implanted in a patient with another medical device that is at least capable of delivering RV pacing pulses. LV pacemaker 14 controls LV pacing pulses based on detecting the RV pacing pulses delivered by the other medical device to provide LV leading pacing pulses when both the LV and the RV are paced in a cardiac cycle. The techniques disclosed herein for controlling LV leading pacing pulses improve the performance of pacemaker 14 by enabling the order of LV and RV pacing pulses to be controlled in a way that improves the effectiveness of the CRT or other pacing therapy being delivered. By improving the performance of LV pacemaker 14 in the capability of delivering and controlling LV pacing pulses that lead RV pacing pulses according to the techniques disclosed herein, LV pacemaker 14 is capable of delivering a wider variety of pacing therapies and/or more effective pacing therapy to treat various cardiac abnormalities.

Figure 3:
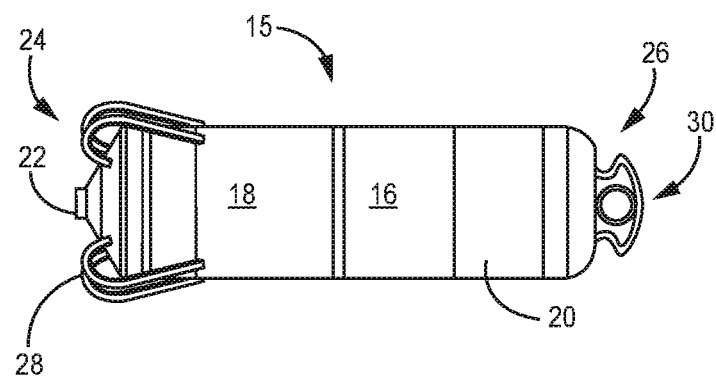
FIG. 3 is a conceptual diagram of the intracardiac left ventricular (LV) pacemaker shown in FIGS. 1 and 2.

FIG. 3 is a conceptual diagram of the intracardiac LV pacemaker 14 shown in FIGS. 1 and 2. Pacemaker 14 includes leadless electrodes 20 and 22 spaced apart on the housing 15 of pacemaker 14 for sensing cardiac electrical signals and delivering pacing pulses. Electrode 22 is shown as a tip electrode extending from a distal end 24 of pacemaker 14, and electrode 20 is shown as a ring electrode along a mid-portion of the lateral wall of housing 15, for example adjacent proximal end 26. Electrode 20 may circumscribe a portion of the lateral sidewall of housing 15 that extends from distal end 24 to proximal end 26. Distal end 24 is referred to as "distal" in that it is expected to be the leading end as pacemaker 14 is advanced through a delivery tool, such as a catheter, and placed against a targeted pacing site.

Electrodes 20 and 22 form an anode and cathode pair for bipolar cardiac pacing and cardiac electrical signal sensing. In alternative embodiments, pacemaker 14 may include two or more ring electrodes, two tip electrodes, and/or other types of electrodes exposed along pacemaker housing 15 for delivering electrical stimulation to heart 8, detecting pacing pulses delivered by another medical device, and sensing cardiac electrical signals. Electrodes 20 and 22 may be positioned at locations along pacemaker 14 other than the locations shown. Electrodes 20 and 22 may be, without limitation, titanium, platinum, iridium or alloys thereof and may include a low polarizing coating, such as titanium nitride, iridium oxide, ruthenium oxide, platinum black among others.

Housing 15 is formed from a biocompatible material, such as a stainless steel or titanium alloy. In some examples, the housing 15 may include an insulating coating. Examples of insulating coatings include parylene, urethane, PEEK, or polyimide among others. The entirety of the housing 15 may be insulated, but only electrodes 20 and 22 uninsulated. Electrode 22 may serve as a cathode electrode and be coupled to internal circuitry, e.g., a pacing pulse generator, pacing pulse detector, and cardiac electrical signal sensing circuitry, enclosed by housing 15 via an electrical feedthrough crossing housing 15. Electrode 20 may be formed as a conductive portion of housing 15 defining a ring electrode that is electrically isolated from the other portions of the housing 150 as generally shown in FIG. 3. In other examples, the entire periphery of the housing 15 may function as an electrode that is electrically isolated from tip electrode 22, instead of providing a localized ring electrode such as anode electrode 20. Electrode 20 defined by an electrically conductive portion of housing 15 serves as a return anode during pacing and sensing.

The housing 15 includes a control electronics subassembly 18, which houses the electronics for sensing cardiac signals, detecting pacing pulses delivered by another medical device, producing pacing pulses and controlling therapy delivery and other functions of pacemaker 14 as described below in conjunction with FIG. 4. Housing 15 further includes a battery subassembly 16, which provides power to the control electronics subassembly 18. Battery subassembly 16 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 14 may include a set of fixation tines 28 to secure pacemaker 14 to patient tissue, e.g., by actively engaging with the ventricular endocardium and/or interacting with the ventricular trabeculae. Fixation tines 28 are configured to anchor pacemaker 14 to position electrode 22 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may include a set of fixation tines as disclosed in commonly-assigned U.S. Pat. No. 9,775,982 (Grubac, et al.), hereby incorporated herein by reference in its entirety.

Pacemaker 14 may optionally include a delivery tool interface 30. Delivery tool interface 30 may be located at the proximal end 26 of pacemaker 14 and is configured to connect to a delivery device, such as a catheter, used to position pacemaker 14 at an implant location during an implantation procedure, for example within the LV.

Figure 4:
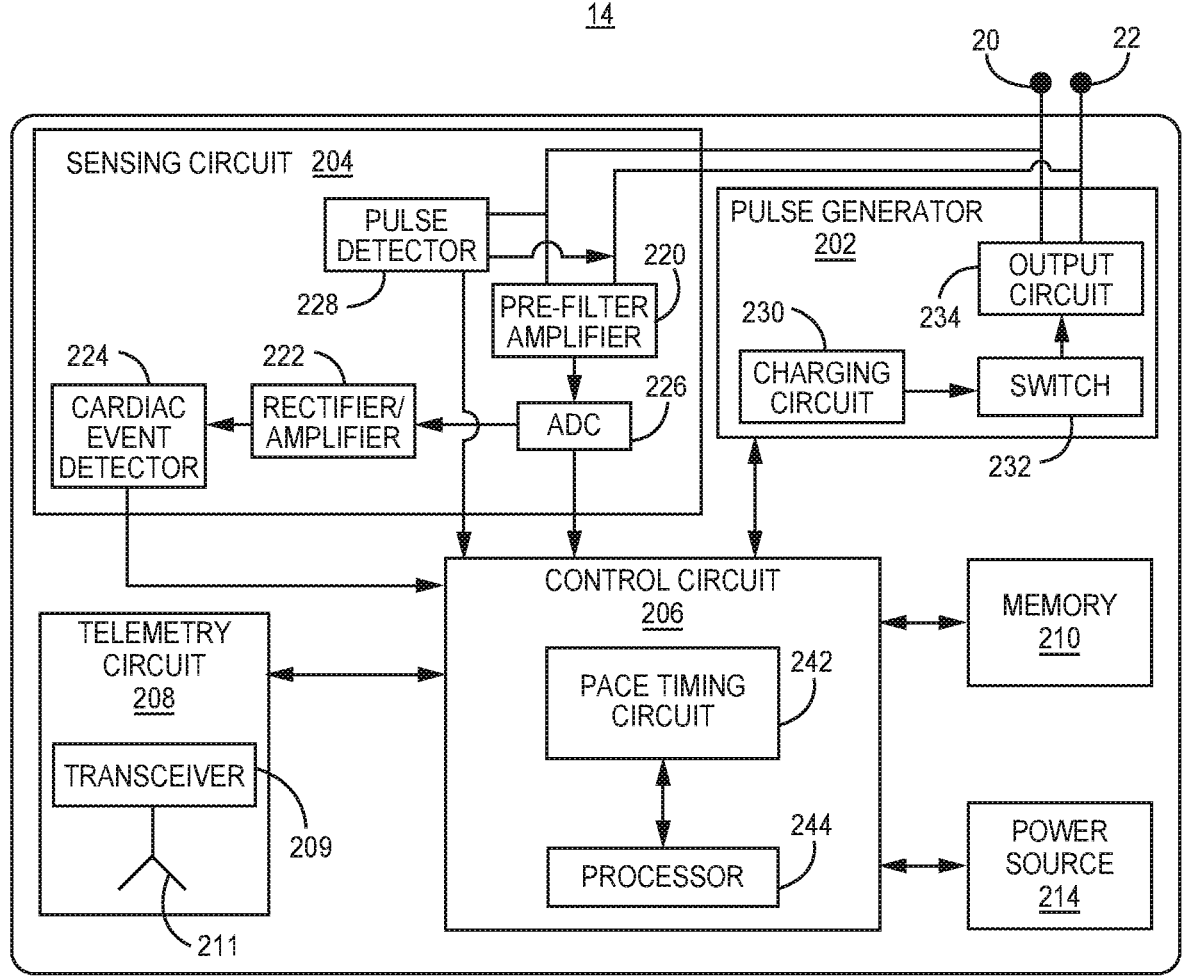
FIG. 4 is a schematic diagram of an example configuration of the LV pacemaker shown in FIG. 3.

FIG. 4 is a schematic diagram of an example configuration of pacemaker 14 shown in FIG. 3. Pacemaker 14 includes a pulse generator 202, a cardiac electrical signal sensing circuit 204 (also referred to herein as "sensing circuit 204") a control circuit 206, memory 210, telemetry circuit 208 and a power source 214. The various circuits represented in FIG. 4 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Cardiac electrical signal sensing circuit 204 is configured to receive a cardiac electrical signal via electrodes 20 and 22 by a pre-filter and amplifier circuit 220. Pre-filter and amplifier circuit may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to ADC 226. ADC 226 may pass a multi-bit, digital electrogram (EGM) signal to control circuit 206 for use in detecting cardiac events and determining a patient's heart rhythm. The digital signal from ADC 226 may be passed to rectifier and amplifier circuit 222, which may include a rectifier, bandpass filter, and amplifier for passing the filtered and rectified cardiac electrical signal to cardiac event detector 224.

Cardiac event detector 224 may include a sense amplifier or other detection circuitry that compares the incoming rectified, cardiac electrical signal to an R-wave detection threshold amplitude, which may be an auto-adjusting threshold. When the incoming signal crosses the R-wave detection threshold, the cardiac event detector 224 produces an R-wave sensed event signal that is passed to control circuit 206. R-wave sensed event signals passed from cardiac event detector 224 to control circuit 206 may be used for scheduling or inhibiting ventricular pacing pulses by pace timing circuit 242 and/or determining ventricular rate intervals or RR intervals (between two consecutively received R-wave sensed event signals).

Sensing circuit 204 includes a pacing pulse detector circuit 228 for detecting cardiac pacing pulses delivered by another medical device. In particular, pulse detector circuit 228 is configured to detect electrical signal spikes in the cardiac electrical signal received by electrodes 20 and 22 that are not physiological in origin, e.g., not R-waves or other intrinsic cardiac electrical signals produced by the depolarization and repolarization of myocardial cells. The electrical signal spikes detectable by pulse detector circuit 228 are characteristic of a pacing pulse delivered by another medical device. For example, electrical signal spikes that meet the frequency, slew rate and/or amplitude of a cardiac pacing pulse may be detected by pulse detector circuit 228 as RV pacing pulses. Such characteristics of frequency, slew rate and amplitude of a cardiac pacing pulse are distinctly different (generally higher) than an intrinsic R-wave, which may not be detectable by pulse detector circuit 228.

For example, pulse detector circuit 228 may include a high pass filter that passes signals that are greater than 100 Hz since intrinsic cardiac signals and other physiological signals are less than 100 Hz. Pulse detector circuit 228 may determine a slew rate, e.g., by a differentiator or first order derivative filter, and compare the slew rate to a threshold slew rate and/or compare an amplitude to an amplitude threshold. Generally, a high amplitude signal that is characterized by a frequency and/or slew rate that is greater than an intrinsic cardiac signal frequency and/or slew rate may be detected as a pacing pulse. Pulse detector circuit 228 may be implemented according to the apparatus and techniques for detecting pacing pulses as generally disclosed in pre-grant U.S. Publication No. 2015/0305642 (Reinke, et al.), incorporated herein by reference in its entirety. Detection of pacing pulses by pulse detector circuit 228 may correspond to the examples generally disclosed in pre-grant U.S. Publication No. 2015/0305640 (Reinke, et al.), incorporated herein by reference in its entirety.

Control circuit 206 includes pace timing circuit 242 and processor 244. Control circuit 206 may receive R-wave sensed event signals and/or digital cardiac electrical signals from sensing circuit 204 for use in detecting and confirming cardiac events and controlling ventricular pacing. For example, R-wave sensed event signals may be passed to pace timing circuit 242 for inhibiting scheduled ventricular pacing pulses. Pace timing circuit 242 (or processor 244) may receive R-wave sensed event signals from cardiac event detector 224 for use in controlling the timing of pacing pulses delivered by pulse generator 202.

Control circuit 206 may retrieve programmable pacing control parameters, such as pacing pulse amplitude and pacing pulse width, which are passed to pulse generator 202 for controlling pacing pulse delivery from memory 210. In addition to providing control signals to pace timing circuit 242 and pulse generator 202 for controlling pacing pulse delivery, control circuit 206 may provide sensing control signals to sensing circuit 204 (e.g., R-wave sensing threshold, sensitivity, and/or various blanking and refractory intervals applied to the cardiac electrical signal).

Pulse generator 202 generates electrical pacing pulses that are delivered to the left ventricle of the patient's heart via cathode electrode 22 and return anode electrode 20. Pulse generator 202 may include charging circuit 230, switching circuit 232 and an output circuit 234. Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of a pacing interval, e.g., an LV pacing escape interval or an RV-LV trigger interval as further described below, and kept closed for a programmed pacing pulse width to enable discharging of the holding capacitor of charging circuit 230. The holding capacitor, previously charged to the pacing pulse voltage amplitude, is discharged across electrodes 20 and 22 through the output capacitor of output circuit 234 for the programmed pacing pulse duration. Examples of pacing circuitry generally disclosed in U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 206 for generating and delivering a pacing pulse.

Memory 210 may include computer-readable instructions that, when executed by control circuit 206, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media. Memory 210 may store timing intervals and other data used by control circuit 206 to control the delivery of pacing pulses by pulse generator 202 according to the techniques disclosed herein.

Power source 214 may correspond to battery subassembly 16 shown in FIG. 3 and provides power to each of the other circuits and components of pacemaker 14 as required. Power source 214 may include one or more energy storage devices, such as one or more rechargeable or non-rechargeable batteries. The connections between power source 214 and other pacemaker circuits and components are not shown in FIG. 4 for the sake of clarity but are to be understood from the general block diagram of FIG. 4. For example power source 214 may provide power to charging circuit 230 for charging a holding capacitor to a pacing voltage amplitude, current to switch 232 and other circuitry included in pulse generator 202 as needed to generate and deliver pacing pulses. Power source 214 also provides power to telemetry circuit 208, sensing circuit 204 as needed as well as memory 210.

Telemetry circuit 208 includes a transceiver 209 and antenna 211 for transferring and receiving data, e.g., via a radio frequency (RF) communication link. Telemetry circuit 208 may be capable of bi-directional communication with external device 40 (FIG. 1) as described above. Cardiac electrical signals, and/or data derived therefrom may be transmitted by telemetry circuit 208 to external device 40. Programmable control parameters and programming commands for performing ventricular pacing control according to the techniques disclosed herein may be received by telemetry circuit 208 and stored in memory 210 for access by control circuit 206.

In some examples, another medical device delivering RV pacing pulses, e.g., RV pacemaker 30 (FIG. 1) or ICD 114 (FIG. 2), may transmit a communication signal contemporaneously with a delivered RV pacing pulse. The communication signal is received by telemetry circuit 208 for detecting RV pacing pulse delivery. Instead of or in addition to having pulse detector circuit 228 for detecting RV pacing pulses delivered by another medical device, telemetry circuit 208 may be configured to detect a communication signal broadcast by another medical device to detect the timing of a delivered RV pacing pulse. Telemetry circuit 208 may transfer the RV pacing pulse detect signal to control circuit 206 for use by processor 244 and pace timing circuit 242 in scheduling a leading LV pacing pulse using the techniques described herein.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, RV pacing pulse detection and LV ventricular pacing control operations performed by pacemaker 14 may be implemented in control circuit 206 executing instructions stored in memory 210 and relying on input from sensing circuit 204.

The operation of circuitry included in pacemaker 14 as disclosed herein should not be construed as reflective of a specific form of hardware, firmware and software necessary to practice the techniques described. It is believed that the particular form of software, hardware and/or firmware will be determined primarily by the particular system architecture employed in the pacemaker 14 and by the particular sensing and therapy delivery circuitry employed by the pacemaker 14. Providing software, hardware, and/or firmware to accomplish the described functionality in the context of any modern pacemaker, given the disclosure herein, is within the abilities of one of skill in the art.

Figure 5:
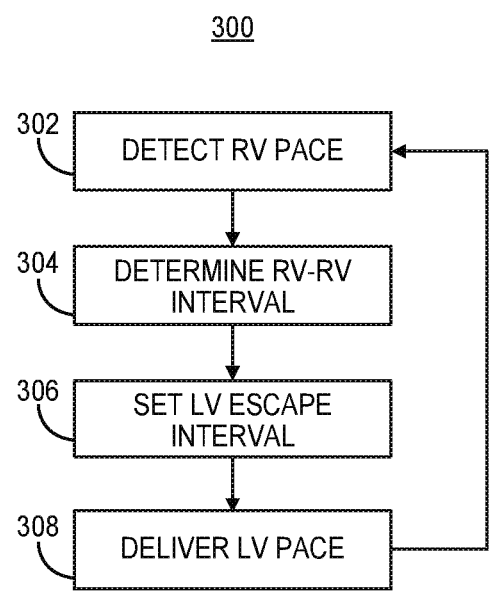
FIG. 5 is a flow chart of a method performed by the LV pacemaker of FIGS. 1 and 2 for delivering leading left ventricular pacing pulses during CRT according to one example.

FIG. 5 is a flow chart 300 of a method performed by pacemaker 14 for delivering leading ventricular pacing pulses during CRT according to one example. In the illustrative examples that follow, pacemaker 14 is assumed to be implanted in the left ventricle to deliver LV pacing pulses that lead RV pacing pulses delivered by another medical device, e.g., RV pacemaker 30 or ICD 114. In these examples, relatively earlier pacing of the left ventricle than the right ventricle in a given cardiac cycle is expected to improve ventricular synchrony, e.g., when the intrinsic contraction of the left ventricle lags the contraction of the right ventricle causing ventricular dyssynchrony.

At block 302, pulse detector circuit 228 detects an RV pacing pulse delivered by another medical device. In other examples, the RV pacing pulse is detected by telemetry circuit 208 by detecting a communication signal that is broadcast by the other medical device at the time that it delivers an RV pacing pulse. Control circuit 206 determines an RV-RV interval at block 304 as the time interval between the detected RV pacing pulse and a most recent preceding detected RV pacing pulse. At block 306, control circuit 206 sets an LV pacing escape interval based on the RV-RV interval. The LV pacing escape interval may be set to the RV-RV interval less an LV pacing pre-interval. The pre-interval is the targeted time interval between a leading LV pacing pulse and the following, lagging RV pacing pulse delivered by another medical device.

The LV pacing escape interval starts upon detection of the RV pacing pulse (or within a minimal processing delay) and expires at the LV pacing pre-interval ahead of the next expected RV pacing pulse. The RV-RV interval determined at block 304 is not expected to change significantly from one pacing cycle to the next so the determined RV-RV interval is expected to be valid in setting an LV pacing escape interval that enables the LV pacing pulse to be delivered before the next expected RV pacing pulse. The LV pacing escape interval may be set based on a single RV-RV interval in some examples and does not require inter-device communication between LV pacemaker 14 and the other device that is delivering RV pacing pulses. Examples of inter-device communication include broadcast radio frequency telemetry signals, other modulated broadcast wireless communication signals and encoded electrical pulses (which may include therapeutic pacing pulses and/or non-therapeutic electrical pulses) that are delivered by the other device to communicate encoded information to the LV pacemaker 14. Such inter-device communication would require demodulation or decoding by the LV pacemaker 14. Instead, pulse detector circuit 228 may detect the delivered, therapeutic RV pacing pulses directly and may determine as few as one RV-RV time interval between two consecutively detected RV pacing pulses for setting the LV pacing escape interval based on the RV-RV time interval for controlling LV pacing pulse timing during CRT or other pacing therapies. By detecting RV pacing pulses directly and utilizing as few as one RV-RV interval, the processing and power burden of analyzing multiple signals or demodulating or decoding signals or pulses produced by another medical device is reduced or eliminated. At block 308, the LV pacing pulse is delivered upon expiration of the LV pacing escape interval. The process returns to block 302 to detect the next RV pacing pulse by RV pulse detector 228 for use in determining the next RV-RV interval and LV pacing escape interval.

Figure 6:
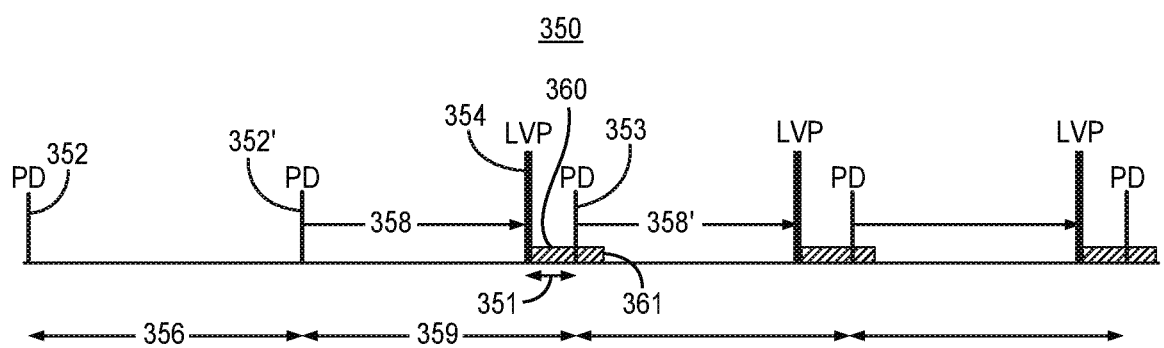
FIG. 6 is a timing diagram illustrating the operation of the LV pacemaker in delivering LV pacing pulses leading RV pacing pulses delivered by a different medical device.

FIG. 6 is a timing diagram 350 illustrating the operation of pacemaker 14, as described in conjunction with FIG. 5, for delivering LV pacing pulses that lead RV pacing pulses delivered by a different implantable device. Control circuit 206 determines the RV-RV interval 356 between two consecutive RV pulse detect (PD) signals 352 and 352' produced by and received from sensing circuit 204. The RV-RV interval 356 determined between two consecutive detected pacing pulses is also referred to herein as a "pulse detect interval." The LV pacing escape interval 358 is set to the RV-RV interval 356 less a desired LV pre-interval 351. The LV pre-interval 351 is the targeted lead time of the LV pacing pulse 354 relative to the next expected RV pacing pulse, represented by pulse detect signal 353 in this example. The LV pre-interval 351 may be 10 to 200 ms, as examples, and may be tailored according to individual patient need. LV pacing pulse 354 is delivered upon expiration of the LV pacing escape interval 358.

Upon delivering the LV pacing pulse 354, control circuit 206 may start a VV window 360 during which the subsequent RV pulse detect signal 353 is expected to occur if the LV pacing pulse 354 is delivered at approximately the desired pre-interval 351 earlier than the RV pacing pulse. VV window 360 is also referred to herein as an "inter-chamber window" in that it is a time interval from the delivered LV pacing pulse 354 until a maximum inter-chamber time interval 361, in this example a maximum LV-RV time interval, that is considered acceptable for achieving ventricular resynchronization. The next pacing pulse delivered to the RV by another medical device is expected to occur within the VV window 360 if the LV pacing pulse and RV pacing pulse are delivered within a maximum desired VV or inter-ventricular time interval 361. If an RV pacing pulse is not detected within the VV interval 360, before the maximum inter-chamber interval 361, the LV pacing pulse 354 may not be properly synchronized to the RV pacing pulses delivered by the other medical device or the RV pacing rate may have unexpectedly changed. When the RV pacing pulse is detected during the VV window 360, as indicated by pulse detect signal 353, proper synchronization of the leading LV pacing pulse 354 to the next RV pacing pulse has been achieved.

The RV-RV interval 359 between the subsequent RV pulse detect signal 353 and the most recent preceding RV pulse detect signal 352' is determined for setting the next LV pacing escape interval 358'. In this way, LV pacing pulses are delivered leading the RV pacing pulses for improving the pacing therapy delivered by the pacemaker 14 by promoting ventricular synchrony.

It is recognized that in some examples, the processing time for determining the RV-RV interval and the LV pacing escape interval based on the RV-RV interval may require a delay of one cardiac cycle before applying an updated LV pacing escape interval. For example, in FIG. 6, the LV pacing escape interval 358' may be based on the RV-RV interval 356 determined one ventricular cycle earlier. Likewise, the LV pacing escape interval 358 may be based on the RV-RV interval (not shown) that would precede RV-RV interval 356, ending with pulse detect signal 352. Since abrupt changes in the RV pacing rate are not expected, a one cycle lag in applying an updated LV pacing escape interval based on a preceding RV-RV interval may be acceptable and still used successfully in achieving LV leading pacing.

Figure 7:
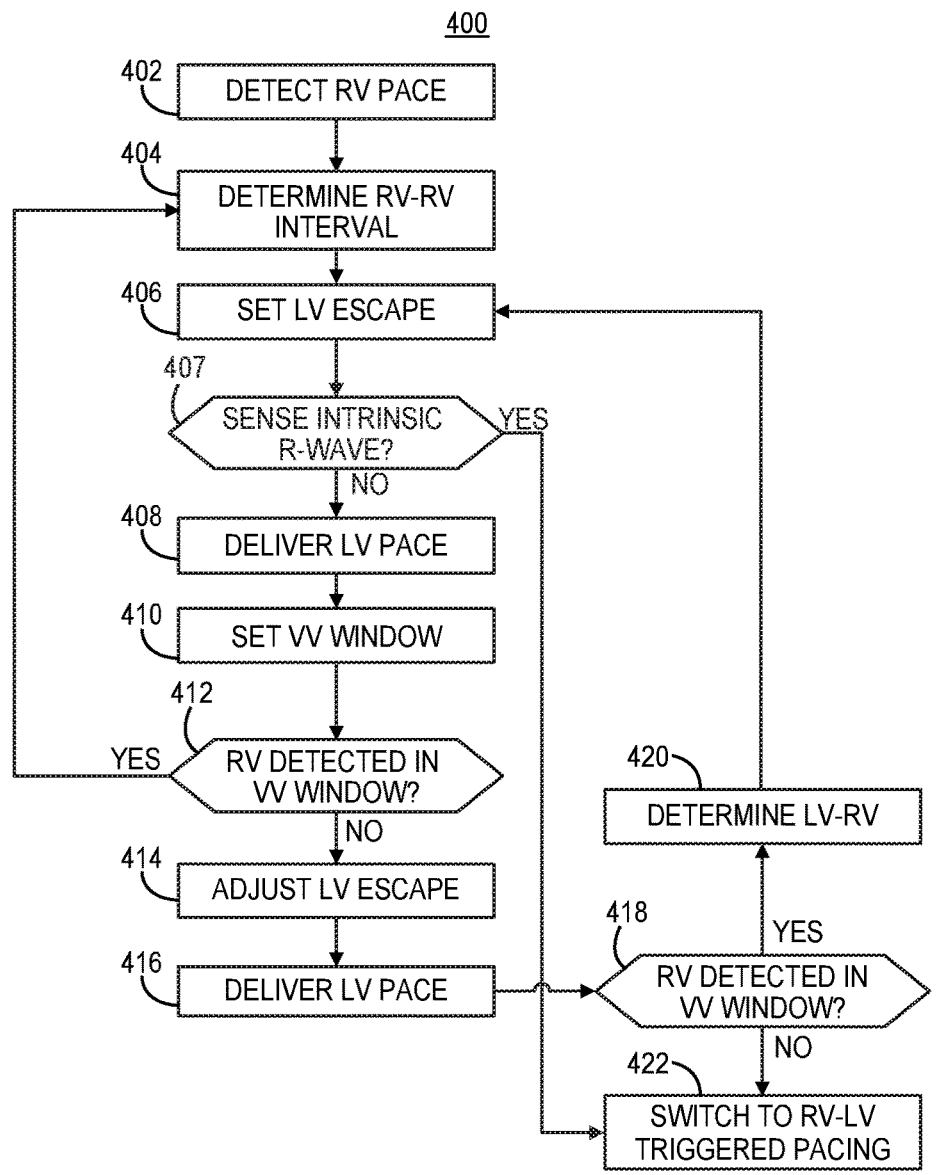
FIG. 7 is a flow chart of a method for controlling pacing pulse delivery by the LV pacemaker according to another example.
Figure 8:
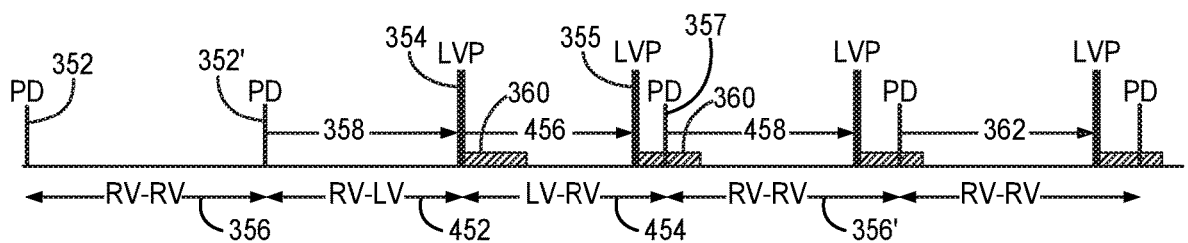
FIG. 8 is a timing diagram of right ventricular (RV) pacing pulse detect signals and LV pacing pulses delivered according to the method of FIG. 7.

FIG. 7 is a flow chart 400 of a method for controlling LV pacing delivery by pacemaker 14 according to another example. FIG. 8 is a timing diagram 450 of RV pulse detect signals and LV pacing pulses delivered according to the method of FIG. 7. With reference to both FIGS. 7 and 8, at block 402, sensing circuit 204 detects an RV pacing pulse delivered by another medical device. Control circuit 206 determines an RV-RV interval 356 between two consecutive RV pulse detect signals 352 and 352' (FIG. 8) received from sensing circuit 204 at block 404 (FIG. 7). Control circuit 206 determines the LV pacing escape interval 358 at block 406 to be an LV pre-interval shorter than the RV-RV interval 356. Control circuit 206 schedules an LV pacing pulse by starting the LV pacing escape interval 358 following the pulse detect signal 352'.

In some instances, sensing circuit 204 may sense an intrinsic R-wave, attendant to an intrinsic ventricular myocardial depolarization, during an LV pacing escape interval, as determined at block 407. Control circuit 206 may respond to the R-wave sensed event signal received from sensing circuit 204 by aborting the scheduled LV pacing pulse and switching to RV-LV triggered pacing at block 422. The RV-LV triggered pacing mode is described below in conjunction with FIG. 9. An LV pacing pulse may be withheld until an RV pacing pulse is detected, triggering delivery of an LV pacing pulse at a relatively short trigger interval. After detecting at least two consecutive RV pacing pulses, control circuit 206 may restart the process of FIG. 7 by determining an updated RV-RV interval at block 404 and setting an LV pacing escape interval at block 406.

When the LV pacing escape interval 358 expires without sensing an intrinsic R-wave ("no" branch of block 407), pulse generator 202 delivers the scheduled LV pacing pulse 354 at block 408 at the expiration of the LV pacing escape interval 358. At block 410, control circuit 206 may set the VV window 360, during which the next RV pulse detect signal is expected to occur. In some cases, the LV pacing pulse may be delivered approximately simultaneously with the RV pacing pulse delivered by another medical device such that the RV pacing pulse is not detected by sensing circuit 204. If the RV pacing pulse is detected in the VV window 360 ("yes" branch of block 412), the process returns to block 404 to determine the RV-RV interval and set the next LV pacing escape interval at block 406. The LV is being paced ahead of the RV at an acceptable pre-interval for promoting ventricular synchrony.

If control circuit 206 does not receive an RV pulse detect signal from sensing circuit 204 during the VV window 360 ("no" branch of block 412), control circuit 206 adjusts the LV pacing escape interval at block 414. As shown in FIG. 8, control circuit 206 may determine the RV-LV interval 452, also referred to herein as a "pulse detect to pulse delivered interval," which preceded the VV window 360 that is absent of an RV pulse detect signal. The adjusted LV pacing escape interval 456 may be set as the RV-LV interval 452 less the desired LV pre-interval. If the LV pacing pulse 354 is delivered at approximately the same time as an RV pacing pulse, interfering with the detection of the RV pacing pulse, the RV-LV interval 452 may be an appropriate estimate of the actual RV-RV interval and can be used for setting the next, adjusted LV pacing escape interval 456.

Pulse generator 202 delivers the next LV pacing pulse 355 at block 416 upon expiration of the shortened LV pacing escape interval 456. The relatively earlier LV pacing pulse 355 is followed by a VV window 360. The next RV pacing pulse detect signal 357 is produced during the VV window 360, with the RV pacing pulse being revealed by delivering the relatively earlier LV pacing pulse 355. Since the preceding LV pacing pulse 354 is suspected of being delivered about simultaneously with an RV pacing pulse, the LV-RV interval 454, also referred to herein as a "delivered pace to detected pace interval," is deemed a reasonable indication of the actual RV-RV interval. This LV-RV interval 454 may be determined by control circuit 206 at block 420 (FIG. 7) and used for setting the next LV pacing escape interval 458 at block 406. The next LV pacing escape interval 458 may be set to the LV-RV interval 454 less the desired LV pre-interval. Pulse generator 202 delivers the next LV pacing pulse upon expiration of the LV pacing escape interval 458.

By shortening the LV pacing escape interval, e.g., based on an RV-LV interval 452 in response to no RV pulse detect signal being received during the VV window 360, the control circuit 206 effectively resets the timing of the next LV pacing pulse 355 to be relatively earlier in the RV-RV interval so that the timing of the next RV pacing pulse delivered by another device is revealed during the VV window 360. After setting the LV pacing escape interval based on one RV-LV interval 452 and one LV-RV interval 454, RV pacing pulse detection during the VV windows following LV pacing pulses is restored. Control circuit 206 may resume setting the LV pacing escape interval 362 based on the RV-RV intervals 356' determined between consecutive RV pulse detection signals.

Returning to FIG. 7, if the RV pacing pulse is not detected during a second consecutive VV window following the LV pacing pulse 355 delivered at the shortened pacing escape interval, "no" branch of block 418, control circuit 206 may switch to delivering LV pacing pulses at a triggered VV interval after RV pulse detect signals (block 422). When the RV pacing pulse is not revealed in a VV window 360 after delivering the LV pacing pulse at an adjusted LV pacing escape interval (based on an RV-LV interval) for one (or more) cycles, pacemaker 14 may have lost tracking of the RV pacing pulses. Instead of continuing to attempt to lead the RV pacing pulse by an LV pacing pre-interval, pacemaker 14 may switch to triggering the LV pacing pulse to follow a detected RV pacing pulse for one or more pacing cycles to regain detection of the RV pacing pulses and tracking of the RV-RV intervals. Switching to triggering the LV pacing pulse to follow a detected RV pacing pulse may be a temporary pacing mode and is referred to herein as an "RV-LV triggered pacing mode" or simply a "triggered pacing mode." Pacemaker operations during the triggered pacing mode in which LV pacing pulses follow detected RV pacing pulses at a relatively short trigger time interval are described below in conjunction with FIGS. 9 and 10.

It is contemplated that if the RV pacing pulse detection signal is not received by the control circuit 206 during one or a higher threshold number of VV windows directly following an LV pacing pulse, the LV pacing escape interval could be increased rather than decreased or a combination of adjustments of the LV pacing escape interval may be made over multiple pacing cycles. One or more adjustments to the LV pacing escape interval may be made to reveal an RV pacing pulse that may be going undetected due to near simultaneous RV and LV pacing pulse delivery. In the example described in conjunction with FIG. 7, the LV pacing escape interval is adjusted by using a different ventricular event interval, e.g., the RV-LV interval rather than the RV-RV interval. In other examples, adjusting the LV pacing escape interval to reveal an undetected RV pacing pulse may include increasing or decreasing the pre-interval that is subtracted from the ventricular event interval used for setting the escape interval. In still other examples, the LV pacing pulse may be withheld until one or more RV pacing pulses are detected to re-establish the RV-RV interval upon which the LV pacing escape interval is based.

Figure 9:
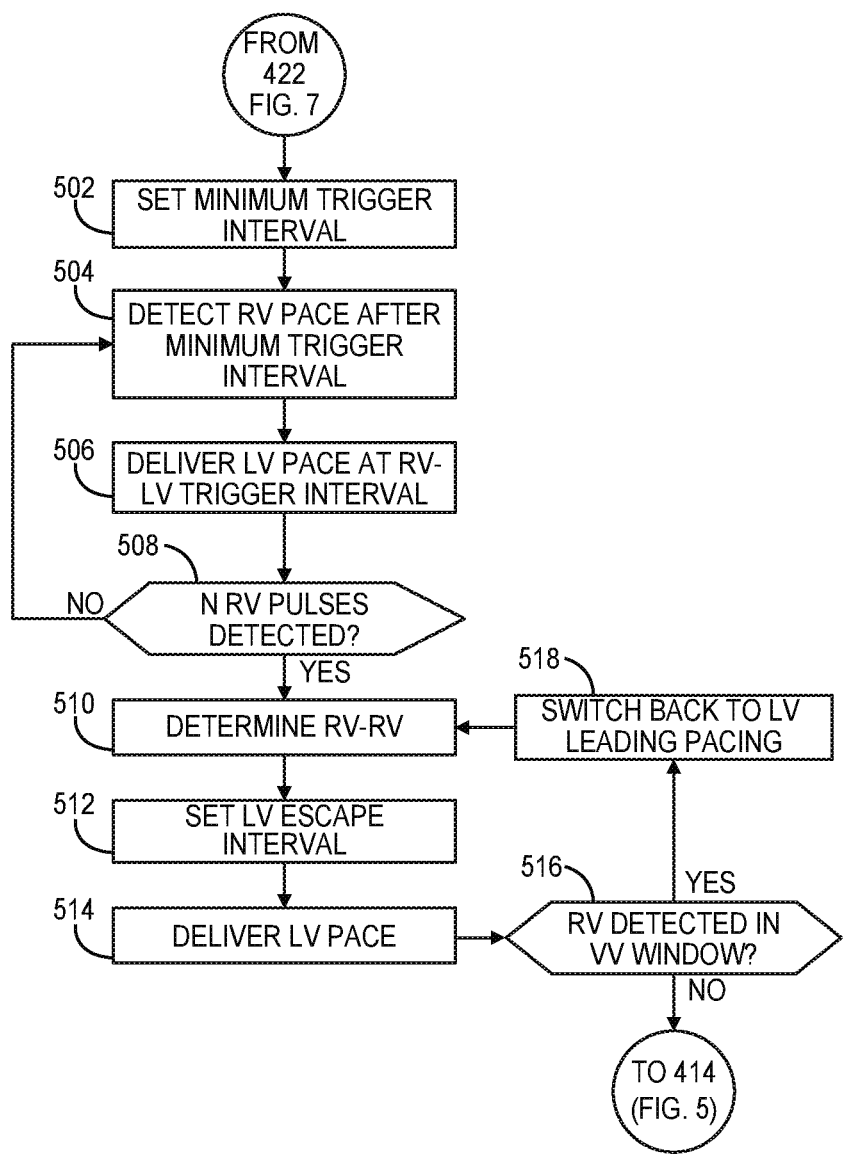
FIG. 9 is a flow chart of a method performed by the LV pacemaker in an RV-LV triggered pacing mode.
Figure 10:
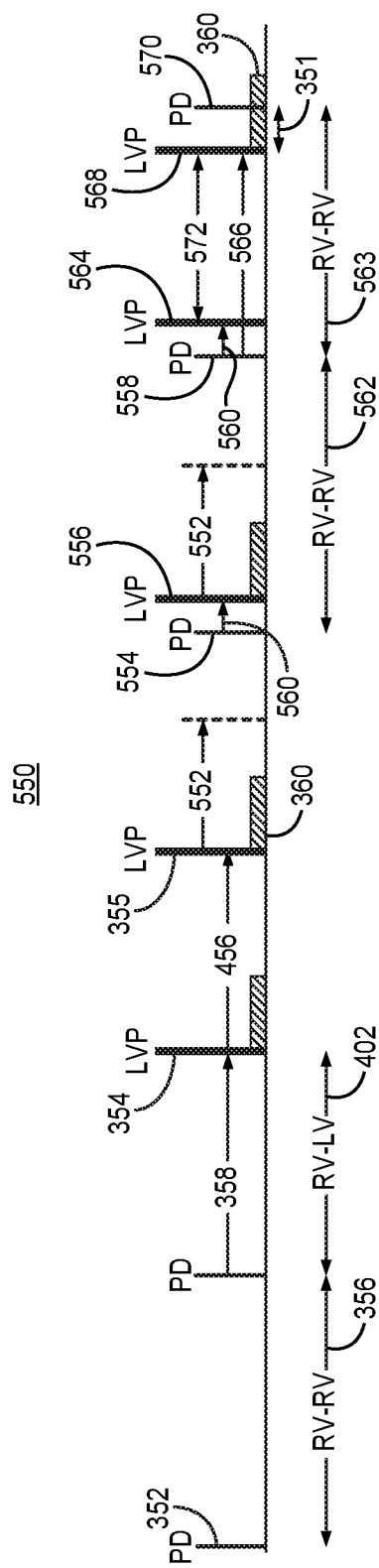
FIG. 10 is a timing diagram of LV pacing pulses and RV pacing pulse detect signals that may occur during the RV-RV triggered pacing mode.

FIG. 9 is a flow chart 500 of a method performed by pacemaker 14 in the triggered pacing mode at block 422 of FIG. 7. FIG. 10 is a timing diagram 550 of LV pacing pulses and RV pacing pulse detect signals that may occur during the triggered pacing mode method of flow chart 500. After delivering LV pacing pulse 355 at a shortened LV pacing escape interval 456, as described above in conjunction with FIG. 8, control circuit 206 switches to the RV-LV triggered pacing mode in response to no RV pacing pulse detect signal received during the next VV interval 360 directly following LV pacing pulse 355. With reference to both FIGS. 9 and 10, at block 502, control circuit 206 sets a minimum trigger interval 552 upon switching to the LV triggered pacing mode. An RV pulse detect signal received from sensing circuit 204 earlier than the expiration of the minimum trigger interval 552 may be ignored by control circuit 206 for the purposes of triggering an LV pacing pulse. An early RV pacing pulse, during minimum trigger interval 552 after LV pacing pulse 355, could cause a triggered LV pacing pulse to be delivered at an unacceptable high rate (short interval) after LV pacing pulse 355. In other examples, an RV pulse detect signal earlier than the expiration of the minimum trigger interval 552 may restart the minimum trigger interval 552, without triggering delivery of an LV pacing pulse.

At block 504 of FIG. 9, sensing circuit 204 detects an RV pacing pulse after the expiration of the minimum trigger interval 552 and passes pulse detect signal 554 to control circuit 206. Control circuit 206 triggers an LV pacing pulse by starting a trigger interval 560 at block 506 in response to receiving the pulse detect signal 554. Trigger interval 560 may be a minimal RV-LV pacing interval to promote as early as possible LV contraction upon detecting the RV pacing pulse. For example, trigger interval 560 may be 0 ms (neglecting any inherent circuit delay) to 50 ms in duration. Pulse generator 202 delivers LV pacing pulse 556 at block 506 in response to the trigger interval 560 expiring.

At least two consecutive RV pacing pulses are required to determine the RV-RV interval for re-establishing an LV pacing escape interval that is a pre-interval shorter than the RV-RV interval for LV-leading biventricular pacing. Accordingly, at block 508, control circuit 206 may determine when at least two, or another threshold number, consecutive RV pacing pulses have been detected during the triggered LV pacing mode.

As shown in FIG. 10, two consecutive LV pacing pulses 556 and 564 are delivered at the trigger interval 560 following respective RV pacing pulse detect signals 554 and 558, each received after the expiration of the minimum trigger interval 552. In response to receiving the two consecutive RV pacing pulse detect signals 554 and 558, control circuit 206 determines the RV-RV interval 562 (block 510, FIG. 9) and sets an LV pacing escape interval 566 (block 512, FIG. 9). The LV pacing escape interval 566 is set to the RV-RV interval 562 less the desired LV pre-interval as described above in conjunction with FIG. 6. LV pacing escape interval 566 is started at pulse detect signal 558. Pulse generator 202 delivers the LV pacing pulse 568 upon expiration of LV pacing escape interval 566, at block 514 of FIG. 9, leading the next RV pacing pulse detect signal 570 by approximately the LV pre-interval 351.

The next RV pacing pulse may be detected during the VV window 360 started by control circuit 206, directly following the leading LV pacing pulse 568. In response to an RV pacing pulse detect signal 570 during the VV window 360 ("yes" branch of block 516), control circuit 206 may return to delivering LV leading pacing at block 518. As long as RV pacing pulse detect signals are received during the VV window 360, RV-RV intervals are determined at block 510 and used to set the LV pacing escape interval at block 512 based on the RV-RV interval less the LV pre-interval. If an RV pacing pulse is not detected during the VV window 360 ("no" branch of block 516), the process may return to block 414 of FIG. 7 to adjust the LV pacing escape interval to restore RV pacing pulse detection RV-RV interval tracking as described above.

In some examples, control circuit 206 may determine the expected LV-LV interval 572 between the last LV pacing pulse 564 triggered to follow an RV pacing pulse detect signal 558 and the first LV pacing pulse 568 scheduled at the LV pacing escape interval 566 to lead the next RV pacing pulse. The expected LV-LV interval 572 may be determined prior to delivering the triggered pacing pulse 564, upon pulse detection signal 558 and determination of RV-RV interval 562. If the expected LV-LV interval 568 is less than a threshold interval, potentially resulting in a rapid left ventricular beat, the LV pacing pulse 564 scheduled at the trigger interval 560 may be withheld and the leading LV pacing pulse 568 may be delivered. In some cases, the trigger interval 560 may be too short to allow a determination of the expected LV-LV interval and comparison to a threshold interval. In this case, triggered LV pacing pulse 564 is delivered and the leading LV pacing pulse 568 may be withheld when the resulting LV-LV interval 572 is less than a threshold interval to avoid a rapid ventricular beat. The next LV pacing pulse may be scheduled at an LV pacing escape interval set based on RV-RV interval 563 between the last triggering pulse detect signal 558 and the next pulse detect signal 570.

By switching to a triggered pacing mode in which the LV pacing pulse is triggered to be delivered at a short interval following the detected RV pacing pulse, tracking of the RV pacing pulses can be restored when RV pulse detect signals are not being detected during the expected VV window following leading LV pacing pulses. Using a minimum trigger interval for triggering LV pulses may help to maintain some degree of ventricular synchrony improvement and optionally withholding an LV pacing pulse during the transition from the triggered pacing mode back to the LV leading pacing mode avoids delivery of an LV pacing pulse at an unacceptably high pacing rate.

Figure 11:
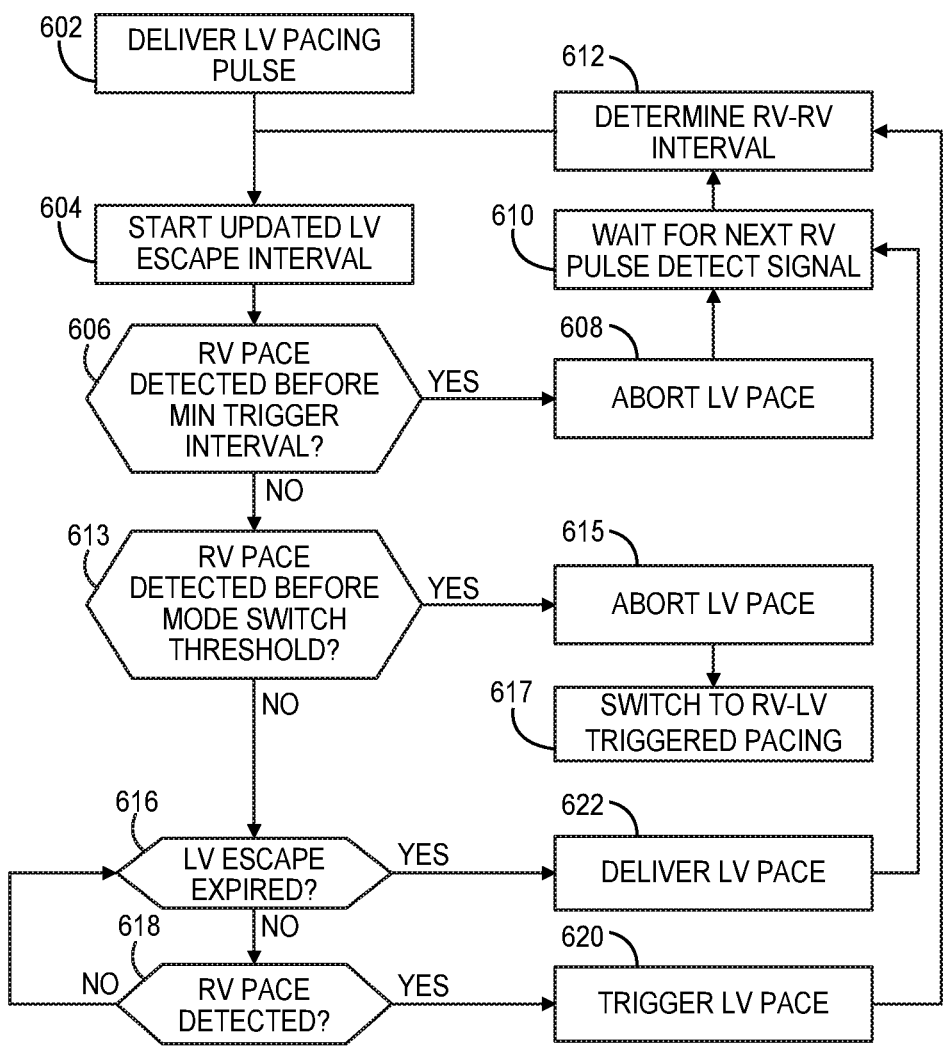
FIG. 11 is a flow chart of a method for delivering pacing pulses by the LV pacemaker according to another example.

FIG. 11 is a flow chart 600 of a method for delivering left ventricular pacing pulses by pacemaker 14 according to another example. FIGS. 12-15 are timing diagrams depicting LV pacing pulses and RV pulse detect signals that may occur during the operations performed according to flow chart 600 of FIG. 11. At block 602, an LV pacing pulse is delivered upon expiration of an LV pacing escape interval set according to the techniques described above in conjunction with FIGS. 5 and 6. As shown in the timing diagram 650 of FIG. 12, the LV pacing pulse 654 is expected to be followed by an RV pacing pulse detect signal 652 produced by sensing circuit 204 during the VV window 660 when the LV pacing pulse 654 is appropriately timed for delivery earlier than the RV pacing pulse delivered by another device, e.g., RV pacemaker 30 or ICD 114. The PD signal 652 and the most recent preceding PD signal are used to determine an RV-RV interval for updating the LV pacing escape interval 658 at block 604 (FIG. 11). When an RV pacing pulse detect signal is not received during VV window 660, control circuit 206 may use the RV-LV interval ending with LV pacing pulse 654 to adjust the LV pacing escape interval 658 as described in conjunction with FIGS. 7 and 8. In either case, an LV pacing escape interval 658 is started after LV pacing pulse 654 for scheduling the next LV pacing pulse.

In some instances, an RV pacing pulse may be detected during the LV pacing escape interval 658, before LV pacing pulse 655 is delivered. The response to an RV pacing pulse detected during the LV pacing escape interval 658 may depend on the relative timing of the pulse detect signal during the LV pacing escape interval 658, e.g., how early or late during the LV pacing escape interval 658 the pulse detect signal is received from sensing circuit 204. Control circuit 206 may set at least one time window after the delivered LV pacing pulse 654, during LV pacing escape interval 658, determine if the next pulse detect signal received from the pulse detector circuit 228 occurs during the time window, and selects a response to the next pulse detect signal based on whether the next pulse detect signal occurs within the time window. In various examples, control circuit 206 selects a first response for controlling delivery of the next LV pacing pulse when the next pulse detect signal is received from the pulse detector circuit during a given time window and selects a second response for controlling delivery of the second pacing pulse in response to the next pulse detect signal being received outside the time window. The first and second responses for controlling the timing of the next LV pacing pulse are different from each other and based on the relative timing of the next pulse detect signal within the LV pacing escape interval when the pulse detect signal is received before the expiration of the LV pacing escape interval.

Figure 12:
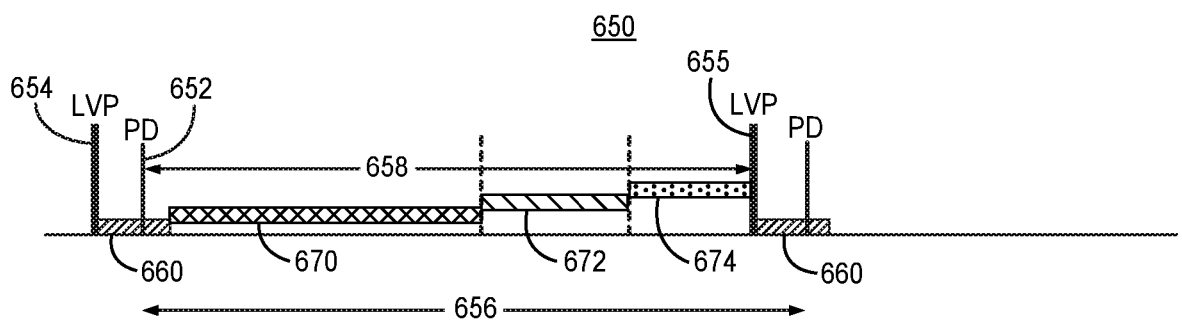
FIG. 12 is a timing diagram depicting multiple timing windows during the LV pacing escape interval for determining the timing of and response to RV pacing pulse detect signals by the LV pacemaker.
Figure 13:
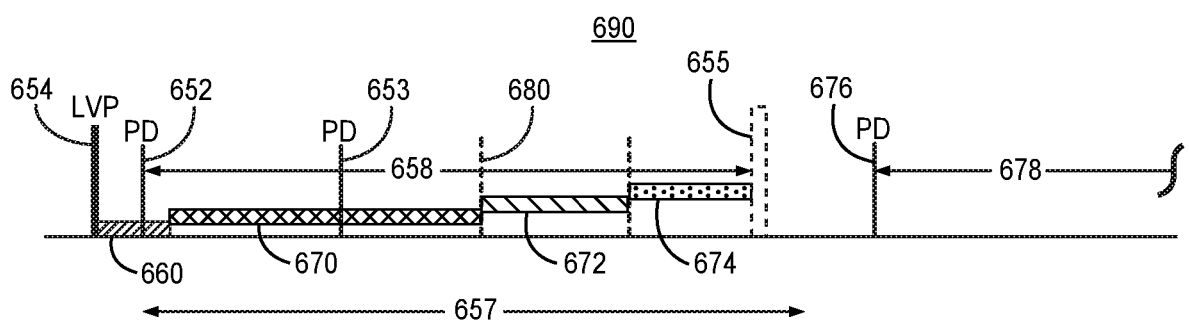
FIG. 13 is a timing diagram depicting the LV pacemaker response to an RV pacing pulse detected earlier than a minimum trigger interval.
Figure 14:
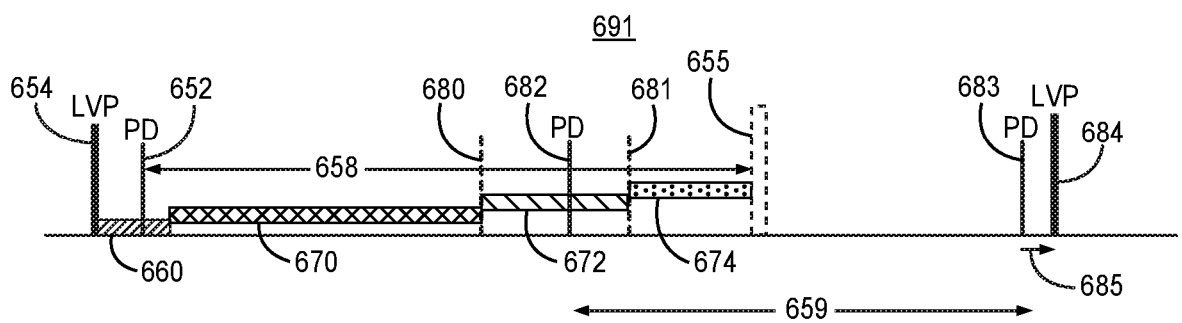
FIG. 14 is a timing diagram depicting the response of the LV pacemaker to an RV pacing pulse being detected during the LV pacing escape interval according to one example.
Figure 15:
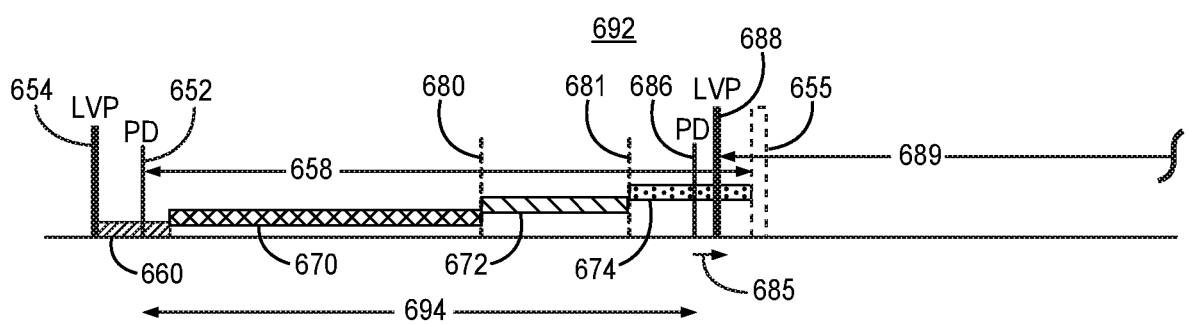
FIG. 15 is a timing diagram depicting the response of the LV pacemaker to an RV pacing pulse detected during the LV pacing escape interval according to another example.

In order to determine the relative timing of a pulse detect signal received during an LV pacing escape interval 658, control circuit 206 may set a number of timers or counters in response to delivery of the LV pacing pulse 654 for establishing multiple time windows 670, 672, and 674 during the LV pacing escape interval 658, following the VV window 660. Flow chart 600 and the timing diagrams of FIGS. 13-15 depict examples of various responses of control circuit 206 selected in response to an RV pacing pulse detect signal that is received from the pulse detector circuit 228 during an LV pacing escape interval. Referring to FIG. 12, when LV pacing escape interval 658 expires without an RV pacing pulse being detected during any of windows 670, 672, or 674, the scheduled LV pacing pulse 655 is delivered. The process of setting VV window 660, determining RV-RV interval 656, and starting an updated LV pacing escape interval and setting subsequent time windows 670, 672 and 675 is repeated.

Referring again to FIG. 11, when control circuit 206 receives an RV pacing pulse detect signal from sensing circuit 204 prior to the expiration of the LV pacing escape interval, however, control circuit 206 may determine if the RV pacing pulse detect signal is received earlier than the minimum trigger interval at block 606. If so, the scheduled LV pacing pulse is aborted at block 608 (the LV pacing escape interval may be cancelled). Control circuit 206 waits for the next RV pulse detect signal at block 610 and determines the next RV-RV interval at block 612 in response to the next RV pulse detect signal. An updated LV pacing escape interval is determined based on the RV-RV interval determined at block 610, and the updated LV pacing escape interval is started at block 604.

This response to an RV pacing pulse detect signal earlier than the minimum trigger interval is depicted in the timing diagram 690 of FIG. 13. LV pacing pulse 654 is followed by a VV window 660 and LV pacing escape interval 658. An RV pacing pulse detect signal 653 is received during window 670, which extends from the expiration of VV window 660 to the minimum trigger time 680. An RV pulse detect signal 653 received during window 670 may indicate a loss of appropriate tracking of the RV pacing rate. Therefore the LV pacing pulse 655 scheduled to be delivered upon expiration of pacing escape interval 658 is withheld.

No other LV pacing pulse is triggered or scheduled in response to pulse detect signal 653. Control circuit 206 waits for the next pulse detect signal 676 and may determine an RV-RV interval 657 between the two consecutive pulse detect signals 653 and 676 for setting an updated LV pacing escape interval 678. In this way, tracking of the RV pacing rate is re-established to enable LV pacing pulses at a pre-interval leading the RV pacing pulses. In other examples, the pulse detect signal 653 may restart the window 670 and subsequent windows 672, and 674. In some cases, pulse detect signal 653 received during window 670 before the minimum trigger time 680 may cause control circuit 206 to restart LV pacing escape interval 658 as well as windows 670, 672 and 674.

Returning to FIG. 11, if an RV pacing pulse detect signal is not detected before the minimum trigger interval ("no" branch of block 606) but is detected before a mode switch threshold time ("yes" branch of block 613), control circuit 206 aborts the scheduled LV pacing pulse at block 615 and switches to the RV-LV triggered pacing mode at block 617. The mode switch threshold time is a maximum time interval after the delivered LV pacing pulse during which a detected RV pacing pulse may cause control circuit 206 to abort the scheduled pacing pulse and switch to the RV-LV triggered pacing mode. An RV pacing pulse detect signal received later than the maximum mode switch threshold time may cause a single triggered LV pacing pulse to be delivered but does not cause control circuit 206 to switch to an RV-LV triggered pacing mode for triggering the next LV pacing pulse after the aborted, scheduled LV pacing pulse (as described below in conjunction with FIG. 15). The RV-LV triggered pacing mode is described above in conjunction with FIGS. 9 and 10.

FIG. 14 is a timing diagram 691 depicting the response of switching to the RV-LV triggered pacing mode by control circuit 206 in response to an RV pacing pulse being detected during the LV pacing escape interval, after the minimum trigger time 680 but before a maximum mode switch threshold time 681. Control circuit 206 may set a mode switch time window 672 starting at the minimum trigger time 680. The mode switch time window 672 may extend from the minimum trigger time 680 to the maximum mode switch threshold time 681. A pulse detect signal 682 received during mode switch time window 672 causes control circuit 206 to abort the scheduled LV pacing pulse 655, which would not be synchronized with the RV pacing pulse detected during window 672. Additionally, control circuit 206 may switch to the RV-LV triggered pacing mode so that upon receiving the next pulse detect signal 683 received after the aborted LV pacing pulse 655 (after expiration of LV pacing escape interval 658), LV pacing pulse 684 is delivered by pulse generator 202 at a trigger interval 685. The RV-RV interval 659 may be determined between consecutive pulse detect signals 682 and 683 to update an LV pacing escape interval. In some examples, the next LV pacing pulse after triggered LV pacing pulse 684 may be delivered at the updated LV pacing escape interval based on RV-RV interval 659, and, if a pulse detect signal is received during the subsequent VV window, control circuit 206 may switch from the RV-LV triggered pacing mode back to the leading LV pacing mode, e.g., as described in conjunction with FIG. 9.

Returning to FIG. 11, if an RV pacing pulse is not detected before the maximum mode switch threshold time at block 613 ("no" branch), and the LV pacing escape interval has not expired ("no" branch of block 616), an RV pacing pulse detect signal received near the end of the LV pacing escape interval, determined at block 618, may cause control circuit 206 to abort the scheduled LV pacing pulse and immediately trigger an LV pacing pulse at block 620. The timing of the scheduled LV pacing pulse may be close to tracking the RV rate, but the RV pacing pulse came slightly earlier than expected at block 618. The early RV pacing pulse detect signal may be used at block 612 to determine an updated RV-RV interval for setting and starting an updated LV pacing escape interval at block 604. After delivery of a single triggered pacing pulse, the control circuit 206 may continue controlling LV pacing pulses in the LV leading pacing mode.

FIG. 15 is a timing diagram 692 depicting the response of control circuit 206 to an RV pacing pulse detect signal 686 being receiving after the maximum mode switch threshold time 681 but before LV pacing escape interval 658 expires. A trigger window 674 extending from the maximum mode switch threshold time 681 until the expiration of the LV pacing escape interval 658 may be set by control circuit 206 to identify RV pacing pulses that are detected near the expiration of the LV pacing escape interval 658. RV pacing pulse detect signals during trigger window 674 may indicate that the RV pacing rate is being closely tracked but the RV pacing pulse came slightly earlier than expected, precluding a leading LV pacing pulse. Control circuit 206 responds to a pulse detect signal 686 during trigger window 674 by aborting the LV pacing pulse scheduled at the expiration of LV pacing escape interval 658 and triggering pulse generator 202 to deliver LV pacing pulse 688 at a trigger interval 685 from the pulse detect signal 686. The triggered LV pacing pulse 688 may not provide optimal ventricular synchrony but may still promote an improvement in ventricular synchrony compared to no LV pacing pulse delivery.

The LV pacing pulse 655 scheduled for delivery at the expiration of LV pacing escape interval 658 is withheld. Control circuit 206 may determine the RV-RV interval 694 between the two consecutive pulse detect signals 652 and 686 and set an updated LV pacing escape interval 689 based on the RV-RV interval 694. It is to be understood that when no pulse detect signal is received during VV window 660, the LV-RV interval between LV pacing pulse 654 and the pulse detect signal 686 may be determined and used to set the updated LV pacing interval 689. Since the LV pacing pulse 688 is a triggered pulse that lags the RV pacing pulse, a VV window 660 is not started by control circuit 206 in response to the triggered pacing pulse 688. However, the timing windows 670, 672, and 674 for distinguishing early RV pacing pulses detected prior to minimum trigger time 680, intermediate RV pacing pulses detected between the minimum trigger time 680 and the maximum mode switch threshold time 681, and relatively late RV pacing pulses detected after mode switch threshold time 681 during the next LV pacing escape interval 689.

Returning to FIG. 11, at block 616, when the LV pacing escape interval expires without an RV pacing pulse detect signal being received during the LV pacing escape interval, the pulse generator 202 delivers the LV pacing pulse as scheduled at block 622. Control circuit 206 waits for the next RV pulse detect signal at block 610, which is expected during the VV window, for updating the RV-RV interval at block 612 and starting an updated LV escape interval at block 604. This response by control circuit 206 to no RV pulse detect signal during the LV pacing escape interval (outside the VV interval 360) is depicted by the timing diagram of FIG. 12. No RV pulse detect signal is received during any of windows 670, 672, or 674, before the expiration of LV pacing escape interval 658. It is to be understood that if the RV pulse detect signal is not received at block 610 during the VV window 660 following the delivered LV pacing pulse 655, control circuit 206 may set a shortened LV pacing escape interval based on the previous RV-LV window (e.g., between pulse detect signal 652 and LV pacing pulse 655) as described in conjunction with FIGS. 7 and 8.

Various examples of responses to an RV pacing pulse detected during an LV pacing escape interval are shown and described in FIGS. 11-15. It is to be understood that one or more various time windows may be defined for determining the relative timing of an RV pacing pulse detect signal received during the LV pacing escape interval. Corresponding responses to an RV pacing pulse detect signal may be selected by control circuit 206 based on whether the RV pacing pulse detect signal is received during a given time window. These responses may include any of the examples given above or combinations thereof. Furthermore, in some examples, not all of the timing windows and responses described in conjunction with FIGS. 11-15 may be provided. One or more timing windows may be set by control circuit 206 after delivering of an LV pacing pulse and/or during the LV pacing escape interval to enable control circuit 206 to select one or more responses or combinations of responses for scheduling the next LV pacing pulse in response to the next RV pacing pulse detect signal.

While not explicitly shown in FIGS. 12-15 and other timing diagrams presented herein, it is recognized that an intrinsic R-wave could be sensed by sensing circuit 204 during the LV pacing escape interval, e.g., during any of the windows 670, 672 or 674. As described above in conjunction with FIG. 7, control circuit 206 may respond to an R-wave sensed event signal received from sensing circuit 204 by cancelling the scheduled LV pacing pulse and switching to the RV-LV triggered pacing mode until detection of RV pacing pulses and tracking of RV-RV intervals can be re-established.

Figure 16:
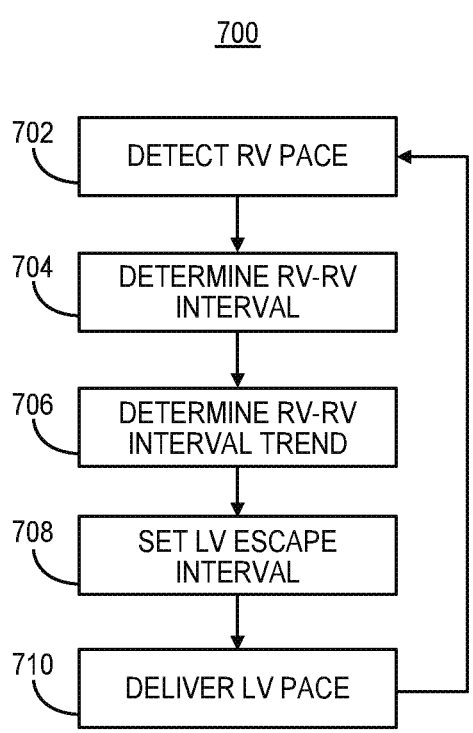
FIG. 16 is a flow chart of a method that may be performed by the LV pacemaker for controlling LV pacing during CRT according to another example.

FIG. 16 is a flow chart 700 of a method performed by LV pacemaker 14 for controlling LV pacing during CRT according to another example. At block 702, sensing circuit 204 detects an RV pacing pulse and produces a pulse detect signal passed to control circuit 206. In response to the RV pacing pulse detect signal, control circuit 206 determines an RV-RV interval extending from the received RV pacing pulse detect signal to the most recent preceding RV pacing pulse detect signal (block 704). Before setting an LV pacing escape interval based on the determined RV-RV interval, control circuit 206 determines an RV-RV interval trend at block 706.

Control circuit 206 may determine the RV-RV interval trend by determining a difference between the current RV-RV interval and the immediately preceding RV-RV interval. In other words the change in the RV-RV interval, ΔRV-RV, may be determined as ΔRV-RV(i)=RV-RV(i)−RV-RV(i−1). This change between two consecutive RV-RV intervals may be determined as the trend in RV-RV interval at block 706 and used to set the LV pacing escape interval at block 708. In other examples, control circuit 206 may compare this change to one or more previously determined changes in the RV-RV interval. For example, a preceding RV-RV interval change may be determined as ΔRV-RV(i−1)=RV-RV(i−1)−RV-RV(i−2), and so on. In some examples, at least two consecutive changes in the RV-RV interval, over at least three consecutively determined RV-RV intervals (requiring at least four detected RV pacing pulses), may be determined and compared at block 706.

When there is no change between two or more consecutive RV-RV intervals, the rate of RV pacing may be determined to be constant. No change between RV-RV intervals may be detected when consecutive RV-RV intervals are within a threshold time difference, e.g., 10 to 20 ms, of each other. The LV pacing escape interval may be set as previously described, based on the most recent RV-RV interval less the LV pre-interval.

If an increasing change is detected, e.g., a positive change between two or more consecutive RV-RV intervals, the average positive change may be added to the LV pacing escape interval set to the currently determined RV-RV interval less the pre-interval. For example, LV pacing escape interval=RV-RV interval−pre-interval+ΔRV-RV(avg), where ΔRV-RV(avg) is the average ΔRV-RV determined over at least three RV-RV intervals. Similarly, when a decreasing change is detected, e.g., a negative change between two or more consecutive RV-RV intervals, the average negative change may be subtracted from the LV pacing escape interval set to the currently determined RV-RV interval less the pre-interval. For example, LV pacing escape interval=RV-RV interval−pre-interval−ΔRV-RV(avg).

After determining the RV-RV interval trend at block 706, control circuit 708 sets the LV pacing escape interval at block 708, based on the most recently determined RV-RV interval, the pre-interval, and the determined trend in RV-RV intervals as just described. Upon expiration of the LV pacing escape interval, pulse generator 202 delivers the LV pacing pulse at block 710. The process of setting the LV pacing escape interval to take into account a constant, increasing, or decreasing trend in RV-RV interval may be used in combination with any of the other techniques disclosed herein. For example, the LV pacing escape interval may be set as described in conjunction with FIG. 16 in combination with selecting a response to a next RV pacing pulse detect signal based on the relative timing of the RV pacing pulse detection during the LV pacing escape interval as described in conjunction with FIGS. 11-15.

ILLUSTRATIVE EMBODIMENTS

While the present disclosure is not so limited, an appreciation of various aspects of the disclosure of the present application will be gained through a discussion of some illustrative embodiments provided below.

In illustrative embodiment 1, a pacemaker includes a pulse detector circuit configured to detect pacing pulses delivered by another medical device and produce a pulse detect signal in response to each one of the detected pacing pulses. The pacemaker includes a control circuit configured to determine a pulse detect interval between two pulse detect signals consecutively received from the pulse detector circuit and set a first pacing escape interval based on the pulse detect interval less a pre-interval. The pacemaker includes a pulse generator configured to deliver a first pacing pulse upon expiration of the first pacing escape interval. The control circuit is further configured to set at least one time window after the delivered first pacing pulse, determine whether a next pulse detect signal is received from the pulse detector circuit during the time window, select a first response for controlling delivery of a second pacing pulse in response to the next pulse detect signal being received during the time window, and select a second response for controlling delivery of the second pacing pulse in response to the next pulse detect signal being received outside the time window, the second response different than the first response.

In illustrative embodiment 2, a method performed by a pacemaker includes detecting, by a pulse detector circuit, pacing pulses delivered by another medical device, producing a pulse detect signal in response to each one of the detected pacing pulses, determining, by a control circuit, a pulse detect interval between two pulse detect signals consecutively produced by the pulse detector circuit, setting a first pacing escape interval based on the pulse detect interval less a pre-interval, delivering, by a pulse generator, a first pacing pulse upon expiration of the first pacing escape interval, setting at least one time window after the delivered first pacing pulse, determining whether a next pulse detect signal is received from the pulse detector circuit during the time window, selecting a first response for controlling delivery of a second pacing pulse in response to the next pulse detect signal being received during the time window, and selecting a second response for controlling delivery of the second pacing pulse in response to the next pulse detect signal being received outside the time window, the second response different than the first response.

In illustrative embodiment 3, a non-transitory, computer-readable storage medium storing a set of instructions which, when executed by a control circuit of a pacemaker, cause the pacemaker to detect pacing pulses delivered by another medical device, produce a pulse detect signal in response to each one of the detected pacing pulses, determine a pulse detect interval between two pulse detect signals consecutively produced by the pulse detector circuit, set a pacing escape interval based on the pulse detect interval less a pre-interval, deliver a pacing pulse upon expiration of the pacing escape interval, set at least one time window after the delivered pacing pulse, determine whether a next pulse detect signal is produced during the time window, select a first response for controlling delivery of a second pacing pulse in response to the next pulse detect signal being produced during the time window, and select a second response for controlling delivery of the second pacing pulse in response to the next pulse detect signal being produced outside the time window, the second response different than the first response.

In illustrative embodiment 4, a device, method or storage medium of any preceding illustrative embodiment is included, wherein setting the at least one time window includes setting a first inter-chamber window extending from the delivered first pacing pulse to a maximum inter-chamber interval and selecting the first response includes updating the pulse detect interval in response to receiving the next pulse detect signal during the inter-chamber window, the control circuit setting a second pacing escape interval based on the updated pulse detect interval less the pre-interval, and the pulse generator delivering the second pacing pulse upon expiration of the second pacing escape interval.

In illustrative embodiment 5, a device, method or storage medium of any preceding illustrative embodiment is included wherein setting the at least one time window includes setting a first inter-chamber window extending from the delivered first pacing pulse to the maximum inter-chamber interval and selecting the second response in response to the next pulse detect signal being received outside the first inter-chamber window includes determining a pulse detect to pulse delivered time interval extending from a most recent preceding pulse detect signal produced by the pulse detector circuit to the delivered first pacing pulse, and further including the control circuit setting a second pacing escape interval based on the pulse detect to pulse delivered time interval less the pre-interval and the pulse generator delivering a second pacing pulse upon expiration of the second pacing escape interval.

In illustrative embodiment 6, a device, method or storage medium of any preceding illustrative embodiment is included, further including the control circuit setting a second inter-chamber window extending from the delivered second pacing pulse to the maximum inter-chamber interval in response to the pulse detector circuit producing a pulse detect signal during the second inter-chamber window, determining a pulse delivered to pulse detect time interval extending from the delivered second pacing pulse to the pulse detect signal produced by the pulse detector circuit during the second inter-chamber window, setting a third pacing escape interval based on the pulse delivered to pulse detect time interval less the pre-interval, and the pulse generator delivering a third pacing pulse upon expiration of the third pacing escape interval.

In illustrative embodiment 7, a device, method or storage medium of any preceding illustrative embodiment is included, wherein setting the at least one time window includes setting an inter-chamber window extending from the delivered first pacing pulse to a maximum inter-chamber interval, selecting the second response includes switching to a triggered pacing mode in response to the next pulse detect signal being received outside the inter-chamber window, and further including the pulse generator delivering a second pacing pulse at a trigger time interval from a pulse detect signal that is produced by the pulse detector circuit after the inter-chamber window expires.

In illustrative embodiment 8, a device, method or storage medium of any preceding illustrative embodiment is included, further including the control circuit scheduling the second pacing pulse by setting a second pacing escape interval after the first pacing pulse, wherein setting the at least one time window includes setting an inter-chamber window extending from the delivered first pacing pulse to a maximum inter-chamber interval, and selecting the second response includes aborting delivery of the scheduled second pacing pulse in response to the next pulse detect signal being received outside the inter-chamber window and during the second pacing escape interval.

In illustrative embodiment 9, a device, method or storage medium of any preceding illustrative embodiment is included, further including the control circuit scheduling a second pacing pulse by setting a second pacing escape interval after the first pacing pulse, setting the at least one time window by setting a mode switch time window starting at a minimum trigger time interval after the first pacing pulse, selecting the first response by aborting the scheduled second pacing pulse and switching to a triggered pacing mode in response to the next pulse detect signal being received during the mode switch time window and during the second pacing escape interval; and the pulse generator delivering a third pacing pulse at a trigger time interval after a pulse detect signal that is produced by the pulse detector circuit after expiration of the second pacing escape interval.

In illustrative embodiment 10, a device, method or storage medium of any preceding illustrative embodiment is included, further including the control circuit scheduling a second pacing pulse by setting a second pacing escape interval after the first pacing pulse, setting the at least one time window by setting a trigger time window starting from a maximum mode switch threshold time interval after the first pacing pulse, selecting the first response in response to the next pulse detect signal being received during the trigger time window by aborting delivery of the scheduled second pacing pulse at an expiration of the second pacing escape interval, and the pulse generator delivering the second pacing pulse at a trigger time interval after the next pulse detect signal received during the trigger time window.

In illustrative embodiment 11, a device, method or storage medium of any preceding illustrative embodiment is included, further including the control circuit scheduling the second pacing pulse by setting a second pacing escape interval after the first pacing pulse, setting a plurality of time windows following the delivered first pacing pulse wherein the plurality of time windows include a first time window corresponding to an expected inter-chamber interval, a second time window following the first time window, a third time window following the second time window and a fourth time window following the third time window, the fourth time window expiring upon expiration of the second pacing escape interval, the control circuit identifying one of the plurality of time windows during which the next pulse detect signal is received from the pulse detector circuit and selecting one of the first response and the second response to the next pulse detect signal according to which one of the plurality of time windows is identified. The selected one of the first response and the second response includes at least one of aborting delivery of the scheduled second pacing pulse at an expiration of the second pacing escape interval and switching to a triggered pacing mode.

In illustrative embodiment 12, a device, method or storage medium of any preceding illustrative embodiment is included, wherein detecting the pacing pulses delivered the other device includes detecting a signal pulse having a frequency and slew rate that exceed a maximum physiological signal frequency and a maximum slew rate threshold, respectively, of an intrinsic cardiac electrical signal.

In illustrative embodiment 13, a device, method or storage medium of any preceding illustrative embodiment is included wherein detecting the pacing pulses delivered by the other medical device includes receiving a pacing pulse communication signal broadcast by the other medical device and detecting the pacing pulse communication signals by a telemetry circuit comprising a receiver.

In illustrative embodiment 14, a device, method or storage medium of any preceding illustrative embodiment is included, further including detecting by a sensing circuit an intrinsic R-wave attendant to an intrinsic myocardial depolarization, switching to a triggered pacing mode in response to the cardiac electrical signal sensing circuit detecting the intrinsic R-wave before the expiration of the first pacing escape interval, withholding the first pacing pulse in response to the cardiac electrical signal sensing circuit detecting the intrinsic R-wave before the expiration of the first pacing escape interval, and responsive to switching to the triggered pacing mode, delivering the second pacing pulse at a trigger time interval from the next pulse detect signal that is produced by the pulse detector circuit.

In illustrative embodiment 15, a device, method or storage medium of any preceding illustrative embodiment is included, further including the control circuit determining an average pulse detect interval change by comparing at least the pulse detect interval to at least one previously determined pulse detect interval, and setting the first pacing escape interval based on the pulse detect interval less the pre-interval plus the average pulse detect interval change.

In illustrative embodiment 16, a device, method or storage medium of any preceding illustrative embodiment is included, wherein delivering the first pacing pulse comprises delivering the first pacing pulse via a pair of leadless electrodes coupled to the pulse generator and on a housing enclosing the pulse detector circuit, the control circuit and the pulse generator and detecting the pacing pulses from a signal received by the pair of leadless electrodes.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a pacemaker has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A leadless pacemaker adapted to stimulate the left ventricle of a heart comprising: a pulse detector circuit configured to detect pacing pulses delivered by another medical device and produce a pulse detect signal in response to each one of the detected pacing pulses; a control circuit configured to: determine a pulse detect interval between two pulse detect signals consecutively received from the pulse detector circuit; set a first pacing escape interval based on the pulse detect interval less a pre-interval; and a pulse generator configured to deliver a first pacing pulse upon expiration of the first pacing escape interval, the control circuit further configured to: set at least one time window after the delivered first pacing pulse; determine whether a next pulse detect signal is received from the pulse detector circuit during the time window; select a first response for controlling delivery of a second pacing pulse in response to the next pulse detect signal being received during the time window; and select a second response for controlling delivery of the second pacing pulse in response to the next pulse detect signal being received outside the time window, the second response different than the first response.

2. The pacemaker of claim 1, wherein:
the control circuit is configured to:
set the at least one time window by setting a first inter-chamber window extending from the delivered first pacing pulse to a maximum inter-chamber interval;
select the first response by updating the pulse detect interval in response to receiving the next pulse detect signal during the inter-chamber window; and
set a second pacing escape interval based on the updated pulse detect interval less the pre-interval; and
the pulse generator is configured to deliver the second pacing pulse upon expiration of the second pacing escape interval.

3. The pacemaker of claim 1, wherein:
the control circuit is further configured to:
set the at least one time window by setting a first inter-chamber window extending from the delivered first pacing pulse to the maximum inter-chamber interval;
select the second response in response to the next pulse detect signal being received outside the first inter-chamber window by determining a pulse detect to pulse delivered time interval extending from a most recent preceding pulse detect signal produced by the pulse detector circuit to the delivered first pacing pulse; and
set a second pacing escape interval based on the pulse detect to pulse delivered time interval less the pre-interval; and
the pulse generator is further configured to deliver the second pacing pulse upon expiration of the second pacing escape interval.

4. The pacemaker of claim 3, wherein:
the control circuit is further configured to:
set a second inter-chamber window extending from the delivered second pacing pulse to the maximum inter-chamber interval;
in response to the pulse detector circuit producing a pulse detect signal during the second inter-chamber window, determine a pulse delivered to pulse detect time interval extending from the delivered second pacing pulse to the pulse detect signal produced by the pulse detector circuit during the second inter-chamber window; and
set a third pacing escape interval based on the pulse delivered to pulse detect time interval less the pre-interval; and
the pulse generator is further configured to deliver a third pacing pulse upon expiration of the third pacing escape interval.

5. The pacemaker of claim 1, wherein:
the control circuit is configured to:
set the at least one time window by setting set an inter-chamber window extending from the delivered first pacing pulse to a maximum inter-chamber interval; and
select the second response by switching to a triggered pacing mode in response to the next pulse detect signal being received outside the inter-chamber window; and
the pulse generator is configured to deliver the second pacing pulse at a trigger time interval from a pulse detect signal that is produced by the pulse detector circuit after the inter-chamber window expires.

6. The pacemaker of claim 1, wherein:
the control circuit is further configured to:
schedule the second pacing pulse by setting a second pacing escape interval after the first pacing pulse;
set the at least one time window by setting set an inter-chamber window extending from the delivered first pacing pulse to a maximum inter-chamber interval; and
select the second response by aborting delivery of the scheduled second pacing pulse in response to the next pulse detect signal being received outside the inter-chamber window and during the second pacing escape interval.

7. The pacemaker of claim 1, wherein:
the control circuit is further configured to:
schedule a second pacing pulse by setting a second pacing escape interval after the first pacing pulse;
set the at least one time window by setting a mode switch time window starting at a minimum trigger time interval after the first pacing pulse; and
select the first response by aborting the scheduled second pacing pulse and switching to a triggered pacing mode in response to the next pulse detect signal being received during the mode switch time window and during the second pacing escape interval; and
the pulse generator is further configured to deliver a third pacing pulse at a trigger time interval after a pulse detect signal that is produced by the pulse detector circuit after expiration of the second pacing escape interval.

8. The pacemaker of claim 1, wherein:
the control circuit is further configured to:
schedule a second pacing pulse by setting a second pacing escape interval after the first pacing pulse;
set the at least one time window by setting a trigger time window starting from a maximum mode switch threshold time interval after the first pacing pulse;
select the first response in response to the next pulse detect signal being received during the trigger time window by aborting delivery of the second pacing pulse at an expiration of the second pacing escape interval; and
the pulse generator is further configured to deliver the second pacing pulse at a trigger time interval after the next pulse detect signal received during the trigger time window.

9. The pacemaker of claim 1, wherein the control circuit is further configured to:
schedule the second pacing pulse by setting a second pacing escape interval after the first pacing pulse;
set a plurality of time windows following the delivered first pacing pulse, the plurality of time windows comprising a first time window corresponding to an expected inter-chamber interval, a second time window following the first time window, a third time window following the second time window, and a fourth time window following the third time window, the fourth time window expiring upon expiration of the second pacing escape interval;

identify one of the plurality of time windows during which the next pulse detect signal is received from the pulse detector circuit; and select one of the first response and the second response to the next pulse detect signal according to which one of the plurality of time windows is identified, wherein the selected one of the first response and the second response includes one of:

aborting delivery of the scheduled second pacing pulse at an expiration of the second pacing escape interval; and switching to a triggered pacing mode.

10. The pacemaker of claim 1, wherein the pulse detector circuit comprises at least one of a high pass filter, a differentiator and a comparator for detecting the pacing pulses delivered by the other device by detecting signal pulses having a frequency and slew rate that exceed a maximum physiological signal frequency and a maximum slew rate threshold, respectively, of an intrinsic cardiac electrical signal.

11. The pacemaker of claim 1, wherein the pulse detector circuit includes a telemetry circuit comprising a receiver configured to receive a pacing pulse communication signal broadcast by the other medical device.

12. The pacemaker of claim 1, further comprising:
a cardiac electrical signal sensing circuit configured to detect an intrinsic R-wave attendant to an intrinsic myocardial depolarization,
wherein the control circuit is further configured to switch to a triggered pacing mode in response to the cardiac electrical signal sensing circuit detecting the intrinsic R-wave before the expiration of the first pacing escape interval;
wherein the pulse generator is configured to withhold the first pacing pulse in response to the cardiac electrical signal sensing circuit detecting the intrinsic R-wave before the expiration of the first pacing escape interval; and
responsive to the control circuit switching to the triggered pacing mode, deliver the second pacing pulse at a trigger time interval from the next pulse detect signal that is produced by the pulse detector circuit.

13. The pacemaker of claim 1, wherein the control circuit is configured to:
determine an average pulse detect interval change by comparing the pulse detect interval to at least one previously determined pulse detect interval; and
set the first pacing escape interval based on the pulse detect interval less the pre-interval plus the average pulse detect interval change.

14. The pacemaker of claim 1, further comprising:
a housing enclosing the pulse detector circuit, the control circuit and the pulse generator; and
a pair of leadless electrodes on the housing and coupled to the pulse generator for delivering the first pacing pulse;
the pair of leadless electrodes being coupled to the pulse detector circuit for detecting the pacing pulses delivered by the other medical device from a signal received by the pair of leadless electrodes.

15. A method performed by a leadless pacemaker adapted to stimulate the left ventricle of a heart, the method comprising: detecting, by a pulse detector circuit, pacing pulses delivered by another medical device; producing a pulse detect signal in response to each one of the detected pacing pulses; determining, by a control circuit, a pulse detect interval between two pulse detect signals consecutively produced by the pulse detector circuit; setting a first pacing escape interval based on the pulse detect interval less a pre-interval; delivering, by a pulse generator, a first pacing pulse upon expiration of the first pacing escape interval; setting at least one time window after the delivered first pacing pulse; determining whether a next pulse detect signal is received from the pulse detector circuit during the time window; selecting a first response for controlling delivery of a second pacing pulse in response to the next pulse detect signal being received during the time window; and selecting a second response for controlling delivery of the second pacing pulse in response to the next pulse detect signal being received outside the time window, the second response different than the first response.

16. The method of claim 15, further comprising:
setting the at least one time window by setting a first inter-chamber window extending from the delivered first pacing pulse to a maximum inter-chamber interval;
selecting the first response by updating the pulse detect interval in response to receiving the next pulse detect signal during the inter-chamber window;
setting a second pacing escape interval to schedule the second pacing pulse based on the updated pulse detect interval less the pre-interval; and
delivering the second pacing pulse upon expiration of the second pacing escape interval.

17. The method of claim 15, further comprising:
setting the at least one time window by setting a first inter-chamber window extending from the delivered first pacing pulse to the maximum inter-chamber interval;
select the second response in response to the next pulse detect signal being received outside the first inter-chamber window by determining a pulse detect to pulse delivered time interval extending from a most recent preceding pulse detect signal produced by the pulse detector circuit to the delivered first pacing pulse;
setting a second pacing escape interval based on the pulse detect to pulse delivered time interval less the pre-interval; and
delivering a second pacing pulse upon expiration of the second pacing escape interval.

18. The method of claim 17, further comprising:
setting a second inter-chamber window extending from the delivered second pacing pulse to the maximum inter-chamber interval;
in response to the pulse detector circuit producing a pulse detect signal during the second inter-chamber window, determining a pulse delivered to pulse detect time interval extending from the delivered second pacing pulse to the pulse detect signal produced by the pulse detector circuit during the second inter-chamber window;
setting a third pacing escape interval based on the pulse delivered to pulse detect time interval less the pre-interval; and
delivering a third pacing pulse upon expiration of the third pacing escape interval.

19. The method of claim 15, further comprising:
setting the at least one time window by setting an inter-chamber window extending from the delivered first pacing pulse to a maximum inter-chamber interval; and
selecting the second response by switching to a triggered pacing mode in response to the next pulse detect signal being received outside the inter-chamber window; and
delivering a second pacing pulse at a trigger time interval from a pulse detect signal that is produced by the pulse detector circuit after the inter-chamber window expires.

20. The method of claim 15, further comprising:
scheduling the second pacing pulse by setting a second pacing escape interval after the first pacing pulse;
setting the at least one time window by setting an inter-chamber window extending from the delivered first pacing pulse to a maximum inter-chamber interval; and
selecting the second response by aborting delivery of the scheduled second pacing pulse in response to the next pulse detect signal being received outside the inter-chamber window and during the second pacing escape interval.

21. The method of claim 15, further comprising:
scheduling a second pacing pulse by setting a second pacing escape interval after the first pacing pulse;
setting the at least one time window by setting a mode switch time window starting at a minimum trigger time interval after the first pacing pulse;
selecting the first response by aborting the scheduled second pacing pulse and switching to a triggered pacing mode in response to the next pulse detect signal being received during the mode switch time window and during the second pacing escape interval; and
delivering a third pacing pulse at a trigger time interval after a pulse detect signal that is produced by the pulse detector circuit after expiration of the second pacing escape interval.

22. The method of claim 15, further comprising:
scheduling a second pacing pulse by setting a second pacing escape interval after the first pacing pulse;
setting the at least one time window by setting a trigger time window starting from a maximum mode switch threshold time interval after the first pacing pulse;
selecting the first response in response to the next pulse detect signal being received during the trigger time window by aborting delivery of the scheduled second pacing pulse at an expiration of the second pacing escape interval; and
delivering the second pacing pulse at a trigger time interval after the next pulse detect signal received during the trigger time window.

23. The method of claim 15, further comprising:
scheduling the second pacing pulse by setting a second pacing escape interval after the first pacing pulse;
setting, by the control module, a plurality of time windows following the delivered first pacing pulse, the plurality of time windows comprising a first time window corresponding to an expected inter-chamber interval, a second time window following the first time window, a third time window following the second time window and a fourth time window following the third time window, the fourth time window expiring upon expiration of the second pacing escape interval;
identifying one of the plurality of time windows during which the next pulse detect signal is received from the pulse detector circuit; and
selecting one of the first response and the second response to the next pulse detect signal according to which one of the plurality of time windows is identified, wherein the selected one of the first response and the second response includes at least one of:
aborting delivery of the scheduled second pacing pulse at an expiration of the second pacing escape interval; and
switching to a triggered pacing mode.

24. The method of claim 15, wherein detecting the pacing pulses delivered the other device comprises detecting a signal pulse having a frequency and slew rate that exceed a maximum physiological signal frequency and a maximum slew rate threshold, respectively, of an intrinsic cardiac electrical signal.

25. The method of claim 15, wherein detecting the pacing pulses delivered by the other medical device comprises:
receiving a pacing pulse communication signal broadcast by the other medical device; and
detecting the pacing pulse communication signals by a telemetry circuit comprising a receiver.

26. The method of claim 15, further comprising:
detecting by a sensing circuit an intrinsic R-wave attendant to an intrinsic myocardial depolarization;
switching to a triggered pacing mode in response to the cardiac electrical signal sensing circuit detecting the intrinsic R-wave before the expiration of the first pacing escape interval;
withholding the first pacing pulse in response to the cardiac electrical signal sensing circuit detecting the intrinsic R-wave before the expiration of the first pacing escape interval; and
responsive to switching to the triggered pacing mode, delivering the second pacing pulse at a trigger time interval from the next pulse detect signal that is produced by the pulse detector circuit.

27. The method of claim 15, further comprising:
determining an average pulse detect interval change by comparing at least the pulse detect interval to at least one previously determined pulse detect interval; and
setting the first pacing escape interval based on the pulse detect interval less the pre-interval plus the average pulse detect interval change.

28. The method of claim 15, wherein:
delivering the first pacing pulse comprises delivering the first pacing pulse via a pair of leadless electrodes coupled to the pulse generator and on a housing enclosing the pulse detector circuit, the control circuit and the pulse generator; and
detecting the pacing pulses from a signal received by the pair of leadless electrodes.

29. A non-transitory, computer-readable storage medium comprising a set of instructions which, when executed by a control circuit of a leadless pacemaker adapted to stimulate the left ventricle of a heart, cause the pacemaker to: detect pacing pulses delivered by another medical device; produce a pulse detect signal in response to each one of the detected pacing pulses; determine a pulse detect interval between two pulse detect signals consecutively produced by the pulse detector circuit; set a pacing escape interval based on the pulse detect interval less a pre-interval; deliver a pacing pulse upon expiration of the pacing escape interval; set at least one time window after the delivered pacing pulse; determine whether a next pulse detect signal is produced during the time window; select a first response for controlling delivery of a second pacing pulse in response to the next pulse detect signal being produced during the time window; and select a second response for controlling delivery of the second pacing pulse in response to the next pulse detect signal being produced outside the time window, the second response different than the first response.

* * * * *